US008483834B2

(12) United States Patent
Lee et al.

(10) Patent No.: US 8,483,834 B2
(45) Date of Patent: *Jul. 9, 2013

(54) METHOD AND APPARATUS FOR CONTROLLING NEURAL STIMULATION DURING DISORDERED BREATHING

(75) Inventors: Kent Lee, Shoreview, MN (US); Imad Libbus, St. Paul, MN (US); Anthony V. Caparso, San Jose, CA (US); Jonathan Kwok, Holmdel, NJ (US); Yachuan Pu, Laguna Niguel, CA (US); Paul A. Haefner, Circle Pines, MN (US); Kristofer J. James, Eagan, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/285,457

(22) Filed: Oct. 31, 2011

(65) Prior Publication Data

US 2012/0046709 A1    Feb. 23, 2012

Related U.S. Application Data

(63) Continuation of application No. 11/468,603, filed on Aug. 30, 2006, now Pat. No. 8,050,765.

(51) Int. Cl.
*A61N 1/08* (2006.01)

(52) U.S. Cl.
USPC .......................................................... 607/42

(58) Field of Classification Search
USPC ........................................ 607/2, 42; 600/529
See application file for complete search history.

(56) References Cited

U.S. PATENT DOCUMENTS

| 4,506,666 | A | 3/1985 | Durkan |
| 4,694,839 | A | 9/1987 | Timme |
| 4,960,129 | A | 10/1990 | dePaola et al. |
| 5,178,156 | A | 1/1993 | Takishima et al. |
| 5,330,507 | A | 7/1994 | Schwartz |
| 5,335,657 | A | 8/1994 | Terry, Jr. et al. |
| 5,591,216 | A | 1/1997 | Testerman et al. |
| 5,954,668 | A | 9/1999 | Uber et al. |
| 6,021,352 | A | 2/2000 | Christopherson et al. |
| 6,141,590 | A | 10/2000 | Renirie et al. |
| 6,240,316 | B1 | 5/2001 | Richmond et al. |
| 6,251,126 | B1 | 6/2001 | Ottenhoff et al. |

(Continued)

FOREIGN PATENT DOCUMENTS

| AU | 2007290623 | | 9/2011 |
| AU | 2007290571 | B2 | 3/2012 |

(Continued)

OTHER PUBLICATIONS

"U.S. Appl. No. 11/468,595 , Response filed Sep. 15, 2011 to Final Office Action mailed Jul. 21, 2011", 9 pgs.

(Continued)

*Primary Examiner* — Tammie K Heller
(74) *Attorney, Agent, or Firm* — Schwegman Lundberg & Woessner, P.A.

(57) ABSTRACT

A neural stimulation system controls the delivery of neural stimulation using a respiratory signal as a therapy feedback input. The respiratory signal is used to increase the effectiveness of the neural stimulation, such as vagal nerve stimulation, while decreasing potentially adverse side effects in respiratory functions. In one embodiment, the neural stimulation system detects apnea and, in response, adjusts the delivery of the neural stimulation pulses and/or delivers a respiratory therapy treating the detected apnea.

20 Claims, 15 Drawing Sheets

U.S. PATENT DOCUMENTS

| | | | |
|---|---|---|---|
| 6,345,202 | B2 | 2/2002 | Richmond et al. |
| 6,442,420 | B1 | 8/2002 | Julu et al. |
| 6,477,418 | B2 | 11/2002 | Plicchi et al. |
| 6,574,507 | B1 | 6/2003 | Bonnet |
| 6,587,725 | B1 | 7/2003 | Durand et al. |
| 6,928,324 | B2 | 8/2005 | Park et al. |
| 7,025,730 | B2 | 4/2006 | Cho et al. |
| 7,277,761 | B2 | 10/2007 | Shelchuk |
| 8,050,765 | B2 | 11/2011 | Lee et al. |
| 8,121,692 | B2 | 2/2012 | Haefner et al. |
| 2001/0010010 | A1 | 7/2001 | Richmond et al. |
| 2002/0107553 | A1 | 8/2002 | Hill et al. |
| 2003/0153953 | A1 | 8/2003 | Park et al. |
| 2003/0195571 | A1 | 10/2003 | Burnes et al. |
| 2003/0199945 | A1 | 10/2003 | Ciulla |
| 2003/0216789 | A1 | 11/2003 | Deem et al. |
| 2004/0111040 | A1 | 6/2004 | Ni et al. |
| 2004/0138719 | A1 | 7/2004 | Cho et al. |
| 2004/0172075 | A1 | 9/2004 | Shafer et al. |
| 2004/0176695 | A1 | 9/2004 | Poezevara |
| 2004/0186523 | A1 | 9/2004 | Florio |
| 2004/0193003 | A1 | 9/2004 | Mechlenburg et al. |
| 2004/0199210 | A1 | 10/2004 | Shelchuk |
| 2004/0210261 | A1 | 10/2004 | King et al. |
| 2004/0249416 | A1 | 12/2004 | Yun et al. |
| 2004/0260356 | A1 | 12/2004 | Kara et al. |
| 2005/0027207 | A1 | 2/2005 | Westbrook et al. |
| 2005/0039745 | A1 | 2/2005 | Stahmann et al. |
| 2005/0043644 | A1 | 2/2005 | Stahmann et al. |
| 2005/0061315 | A1 | 3/2005 | Lee et al. |
| 2005/0061320 | A1 | 3/2005 | Lee et al. |
| 2005/0065566 | A1 | 3/2005 | Hartley et al. |
| 2005/0065575 | A1 | 3/2005 | Dobak |
| 2005/0085865 | A1 | 4/2005 | Tehrani |
| 2005/0085866 | A1 | 4/2005 | Tehrani |
| 2005/0085877 | A1 | 4/2005 | Kratz |
| 2005/0085879 | A1 | 4/2005 | Ahn et al. |
| 2005/0119711 | A1 | 6/2005 | Cho et al. |
| 2005/0137645 | A1 | 6/2005 | Voipio et al. |
| 2005/0143785 | A1 | 6/2005 | Libbus |
| 2005/0148897 | A1 | 7/2005 | Cho et al. |
| 2005/0149127 | A1 | 7/2005 | Libbus |
| 2005/0209643 | A1 | 9/2005 | Heruth et al. |
| 2005/0222066 | A1 | 10/2005 | Richards et al. |
| 2005/0222503 | A1 | 10/2005 | Dunlop et al. |
| 2005/0288729 | A1 | 12/2005 | Libbus et al. |
| 2006/0030897 | A1 | 2/2006 | Gilmer et al. |
| 2006/0036294 | A1 | 2/2006 | Tehrani |
| 2006/0039866 | A1 | 2/2006 | Rao et al. |
| 2006/0058852 | A1 | 3/2006 | Koh et al. |
| 2006/0064137 | A1 | 3/2006 | Stone |
| 2006/0079802 | A1 | 4/2006 | Jensen et al. |
| 2006/0095088 | A1 | 5/2006 | De Ridder |
| 2006/0100668 | A1 | 5/2006 | Ben-David et al. |
| 2006/0111755 | A1 | 5/2006 | Stone et al. |
| 2006/0116737 | A1 | 6/2006 | Libbus |
| 2006/0212081 | A1 | 9/2006 | Suga et al. |
| 2006/0271108 | A1 | 11/2006 | Libbus et al. |
| 2006/0282131 | A1 | 12/2006 | Caparso et al. |
| 2006/0287691 | A1 | 12/2006 | Drew |
| 2008/0058873 | A1 | 3/2008 | Lee et al. |
| 2008/0058892 | A1 | 3/2008 | Haefner et al. |
| 2012/0130446 | A1 | 5/2012 | Haefner et al. |

FOREIGN PATENT DOCUMENTS

| | | |
|---|---|---|
| JP | 6511164 A | 12/1994 |
| JP | 2001505085 A | 4/2001 |
| JP | 2005143829 A | 6/2005 |
| WO | WO-9222348 A1 | 12/1992 |
| WO | WO-9301862 | 2/1993 |
| WO | WO-9514116 A1 | 5/1995 |
| WO | WO-2005102450 A1 | 11/2005 |
| WO | WO-2006002338 A2 | 1/2006 |
| WO | WO-2006050526 A1 | 5/2006 |
| WO | WO-2006055436 A1 | 5/2006 |
| WO | WO-2006127366 A1 | 11/2006 |
| WO | WO-2008027297 A2 | 3/2008 |
| WO | WO-2008027297 A3 | 3/2008 |
| WO | WO-2008027339 A2 | 3/2008 |
| WO | WO-2008027339 A3 | 3/2008 |

OTHER PUBLICATIONS

"U.S. Appl. No. 11/468,595 Non-Final Office Action mailed Aug. 2, 2010", 10 pgs.

"U.S. Appl. No. 11/468,595, Final Office Action mailed Jul. 21, 2011", 5 pgs.

"U.S. Appl. No. 11/468,595, Final Office Action mailed Aug. 7, 2009", 9 pgs.

"U.S. Appl. No. 11/468,595, Non Final Office Action mailed Feb. 4, 2011", 10 pgs.

"U.S. Appl. No. 11/468,595, Non-Final Office Action mailed Feb. 5, 2009", 7 pgs.

"U.S. Appl. No. 11/468,595, Non-Final Office Action mailed Dec. 28, 2009", 11 pgs.

"U.S. Appl. No. 11/468,595, Notice of Allowance mailed Oct. 14, 2011", 6 pgs.

"U.S. Appl. No. 11/468,595, Response filed May 3, 2011 to Non Final Office Action mailed Feb. 4, 2011", 16 pgs.

"U.S. Appl. No. 11/468,595, Response filed May 5, 2009 to Non Final Office Action mailed Feb. 5, 2009", 10 pgs.

"U.S. Appl. No. 11/468,595, Response filed Nov. 2, 2010 to Non Final Office Action mailed Aug. 2, 2010", 13 pgs.

"U.S. Appl. No. 11/468,595, Response filed Nov. 20, 2009 to Final Office Action mailed Aug. 7, 2009", 11 pgs.

"U.S. Appl. No. 11/468,595, Restriction Requirement mailed Jan. 7, 2009", 7 pgs.

"U.S. Appl. No. 11/468,603 Non-Final Office Action mailed Sep. 2, 2010", 13 Pgs.

"U.S. Appl. No. 11/468,603, Advisory Action mailed Jan. 12, 2010", 3 pgs.

"U.S. Appl. No. 11/468,603, Final Office Action mailed Oct. 19, 2009", 14 pgs.

"U.S. Appl. No. 11/468,603, Non-Final Office Action mailed Feb. 24, 2009", 11 pgs.

"U.S. Appl. No. 11/468,603, Notice of Allowance mailed Jul. 27, 2011", 5 pgs.

"U.S. Appl. No. 11/468,603, Notice of Allowance mailed Apr. 14, 2011", 5 pgs.

"U.S. Appl. No. 11/468,603, Response filed Jan. 26, 2011 to Non Final Office Action mailed Sep. 2, 2010", 12 pgs.

"U.S. Appl. No. 11/468,603, Response filed Dec. 14, 2009 to Final Office Action mailed Oct. 19, 2009", 14 pgs.

"U.S. Appl. No. 11/468,603, Response filed Feb. 18, 2010 to Advisory Action mailed Jan. 12, 2010", 14 pgs.

"U.S. Appl. No. 11/468,603, Response filed Jun. 24, 2009 to Non Final Office Action mailed Feb. 24, 2009", 14 pgs.

"U.S. Appl. No. 11/468,595, Response filed Apr. 26, 2010 to Non Final Office Action mailed Dec. 28, 2009", 12 pgs.

"U.S. Appl. No. 12/468,595, Response filed Jan. 26, 2009 to Restriction Requirement mailed Jan. 7, 2009", 8 pgs.

"Australian Application Serial No. 2007290571, First Examiner Report mailed Nov. 16, 2010", 4 Pgs.

"Australian Application Serial No. 2007290571, Response filed Sep. 22, 2011 to Office Action mailed Nov. 16, 2010", 20 pgs.

"Australian Application Serial No. 2007290623, First Examiner Report mailed Aug. 13, 2010", 4 pgs.

"Australian Application Serial No. 2007290623, Response filed May 18, 2011 to First Examiner Report mailed Aug. 13, 2010", 22.

"International Application Serial No. PCT/US2007/018697, International Search Report mailed Mar. 14, 2008", 5 pgs.

"International Application Serial No. PCT/US2007/018697, Written Opinion mailed Mar. 14, 2008", 10 pgs.

"International Application Serial No. PCT/US2007/018846, International Search Report mailed May 27, 2008", 5 pgs.

"International Application Serial No. PCT/US2007/018846, Written Opinion mailed May 27, 2008", 9 pgs.

"Japanese Application Serial No. 2009-526651, Amended Claims filed Aug. 18, 2010", (w/ English Translation of Amended Claims), 11 pgs.

Haefner, Paul A, et al., "Method and Apparatus for Neural Stimulation With Respiratory Feedback", U.S. Appl. No. 11/468,595, filed Aug. 30, 2006, 51 pgs.

Holmes, M. D., et al., "Sleep apnea and excessive daytime somnolence induced by vagal nerve stimulation", Neurology, 6(8), (Oct. 28, 2003), 1126-9.

Kaneko, Y., et al., "Cardiovascular effects of continuous positive airway pressure in patients with heart failure and obstructive sleep apnea.", N Engl J Med., 348(13), (Mar. 27, 2003), 1233-41.

Lee, Kent, et al., "Method and Apparatus for Controlling Neural Stimulation During Disordered Breathing", U.S. Appl. No. 11/468,603, filed Aug. 30, 2006, 48 pgs.

Libbus, Imad, et al., "Neural Stimulator to Treat Sleep Disordered Breathing", U.S. Appl. No. 11/320,500, filed Dec. 28, 2005, 48 pgs.

Libbus, Imad, et al., "System for Abating Neural Stimulation Side Effects", U.S. Appl. No. 11/467,264, filed Aug. 25, 2006, 53 pgs.

Malow, B. A, et al., "Effects of vagus nerve stimulation on respiration during sleep: a pilot study", Neurology, 55(10), (Nov. 28, 2000), 1450-4.

Malow, BA, et al., "Effects of vagus nerve stimulation on respiration during sleep", A pilot study. Neurology 55, (2000), 1450-1454.

Marzec, M., et al., "Effects of vagus nerve stimulation on sleep-related breathing in epilepsy patients", Epilepsia, 44(7), (Jul. 2003), 930-935.

Oldenburg, O., et al., "Central but obstructive sleep apnea can be influenced by cardiac resynchronisation therapy", Heart Rhythm, 2, Abstract, (2005), S98.

Shalaby, A., et al., "Automated detection of sleep apnea using a pacemaker impedance sensor", PACE, 26, Abstract, (2003), 101.

Stahmann, Jeffrey E, "Method and Apparatus for Pulmonary Artery Pressure Signal Isolation", U.S. Appl. No. 11/249,624, filed Oct. 13, 2005, 59 pgs.

Zhang, Yi, et al., "Rapid Shallow Breathing Detection for Use in Congestive Heart Failure Status Determination", U.S. Appl. No. 11/229,316, filed Sep. 16, 2006, 55 pgs.

"Japanese Application Serial No. 2009-526651, Response filed Oct. 3, 2012 to Office Action mailed Jul. 4, 2012", (w/ English Translation of Amended Claims), 7 pgs.

"Japanese Application Serial No. 2009-526671, Response filed Oct. 3, 2012 to Office Action mailed Jul. 4, 2012", (w/ English Translation of Amended Claims), 9 pgs.

"U.S. Appl. No. 13/363,198, Examiner Interview Summary mailed Jul. 25, 2012", 3 pgs.

"U.S. Appl. No. 13/363,198, Non Final Office Action mailed Apr. 4, 2012", 7 pgs.

"U.S. Appl. No. 13/363,198, Response filed Jul. 25, 2012 to Non Final Office Action mailed Apr. 4, 2012", 10 pgs.

"Japanese Application Serial No. 2009-526651, Office Action mailed Jul. 4, 2012", With English Translation, 7 pgs.

"Japanese Application Serial No. 2009-526651, Office Action mailed Jul. 18, 2012", 7 pgs.

"Japanese Application Serial No. 2009-526671, Office Action mailed Jul. 4, 2012", With English Translation, 15 pgs.

METHOD AND APPARATUS FOR CONTROLLING NEURAL STIMULATION DURING DISORDERED BREATHING

CLAIM OF PRIORITY

This application is a continuation of and claims the benefit of priority under 35 U.S.C. §120 to U.S. patent application Ser. No. 11/468,603, entitled "METHOD AND APPARATUS FOR CONTROLLING NEURAL STIMULATION DURING DISORDERED BREATHING," filed on Aug. 30, 2006, now issued as U.S. Pat. No. 8,050,765, which is hereby incorporated by reference herein in its entirety.

CROSS-REFERENCE TO RELATED APPLICATIONS

This application is related to commonly assigned U.S. patent application Ser. No. 11/467,264, entitled "SYSTEM FOR ABATING NEURAL STIMULATION SIDE EFFECTS," filed on Aug. 25, 2006, now issued as U.S. Pat. No. 8,103,341, and U.S. patent application Ser. No. 11/468,595, entitled "METHOD AND APPARATUS FOR NEURAL STIMULATION WITH RESPIRATORY FEEDBACK," filed on Aug. 30, 2006, now issued as U.S. Pat. No. 8,121,692, which are hereby incorporated by reference in their entirety.

TECHNICAL FIELD

This document relates generally to neural stimulation and particularly to a system for controlling neural stimulation during disordered breathing.

BACKGROUND

Electrical stimulation of the autonomic nervous system has been applied to modulate various physiologic functions. One example is the modulation of cardiac functions and hemodynamic performance using neural stimulation. The myocardium is innervated with sympathetic and parasympathetic nerves. Activities in these nerves, including artificially applied electrical stimuli, modulate the heart rate and contractility (strength of the myocardial contractions). Electrical stimulation applied to the parasympathetic nerves, such as the cardiac branch of the vagus nerve, is known to decrease the heart rate and the contractility, lengthen the systolic phase of a cardiac cycle, and shorten the diastolic phase of the cardiac cycle. Electrical stimulation applied to the sympathetic nerves is known to have essentially the opposite effects.

The ability of the electrical stimulation of the autonomic nerves in modulating the heart rate and contractility is utilized to treat abnormal cardiac conditions, such as to improve hemodynamic performance for heart failure patients and to control myocardial remodeling and prevent arrhythmias following myocardial infarction. However, the autonomic nervous system regulates functions of many organs of the body. Neural stimulation pulses delivered to the autonomic nervous system to treat a cardiac disorder may unintentionally modulate various other physiologic functions. Therefore, there is a need to prevent or control unintended, potentially adverse effects when neural stimulation is applied to the autonomic nervous system.

SUMMARY

A neural stimulation system controls the delivery of neural stimulation using a respiratory signal as a therapy feedback input. The respiratory signal is used to increase the effectiveness of the neural stimulation, such as vagal nerve stimulation, while decreasing potentially adverse side effects in respiratory functions.

In one embodiment, a neural stimulation system includes a therapy output device, a therapy delivery controller, a respiratory signal input, a respiratory disorder detector, and a therapy adjustment module. The therapy output device delivers one or more therapies and includes a non-respiratory stimulation output circuit to deliver a neural stimulation therapy treating a non-respiratory disorder. The therapy delivery controller controls the delivery of the one or more therapies and includes a non-respiratory stimulation delivery controller to control the delivery of the neural stimulation therapy. The respiratory signal input receives a respiratory signal. The respiratory disorder detector includes an apnea detector to detect apnea using the respiratory signal. The therapy adjustment module adjusts the delivery of at least one of the one or more therapies in response to the detection of apnea.

In one embodiment, a method for neural stimulation is provided. One or more therapies, including a neural stimulation therapy treating a non-respiratory disorder, are delivered. A respiratory signal is sensed. Apnea is detected using the respiratory signal. The delivery of at least one of the one or more therapies is adjusted in response to the detection of apnea.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof. The scope of the present invention is defined by the appended claims and their legal equivalents.

BRIEF DESCRIPTION OF THE DRAWINGS

The drawings illustrate generally, by way of example, various embodiments discussed in the present document. The drawings are for illustrative purposes only and may not be to scale.

DETAILED DESCRIPTION

Figure 1:
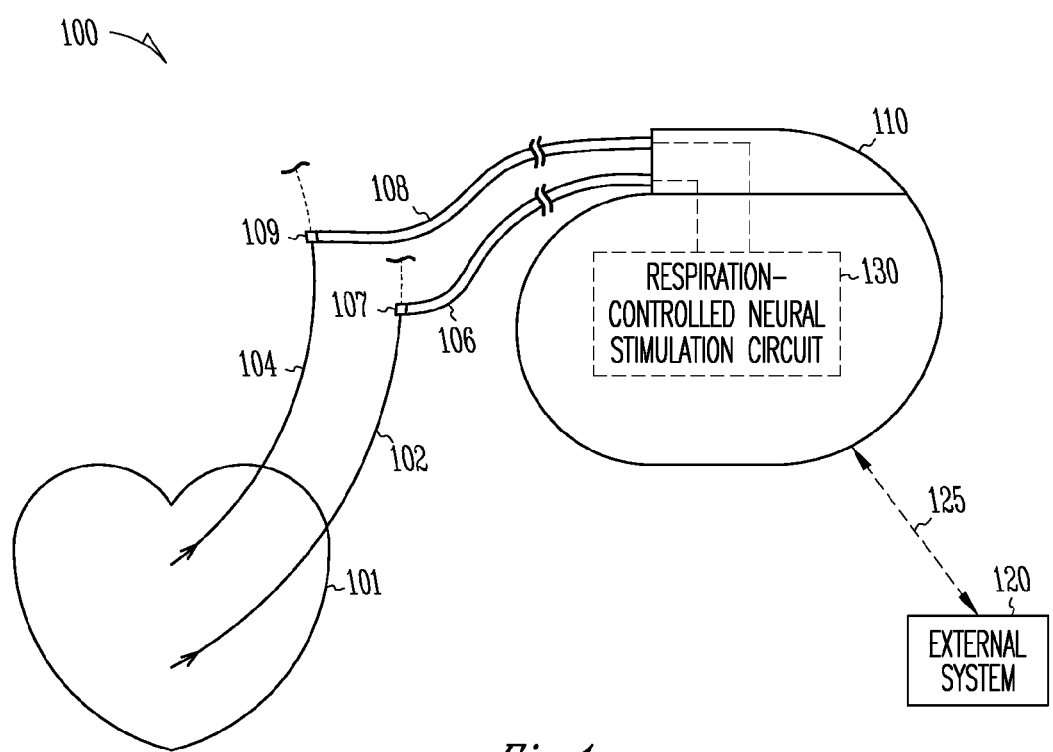
FIG. 1 is an illustration of an embodiment of a neural stimulation system and portions of an environment in which the neural stimulation system is used.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. References to "an", "one", or "various" embodiments in this disclosure are not necessarily to the same embodiment, and such references contemplate more than one embodiment. The following detailed description provides examples, and the scope of the present invention is defined by the appended claims and their legal equivalents.

The relationship between a respiratory rate and a respiratory cycle length (also known as breathing interval), as used in this document, is the relationship between a frequency and its corresponding period. If a respiratory rate is given in breaths per minute, its corresponding respiratory cycle length in seconds is calculated by dividing 60 by the respiratory rate (where 60 is the number of seconds in a minute). Any process, such as a comparison, using a respiratory rate is to be modified accordingly when a respiratory cycle length is used instead. For example, if a low respiratory rate is detected when the respiratory rate falls below a threshold rate, an equivalent process is to detect the low respiratory rate when the respiratory cycle length exceeds a corresponding threshold interval. The appended claims should be construed to cover such variations.

This document discusses a neural stimulation system that synchronizes delivery of neural stimulation to respiratory cycles and/or adjusts delivery of neural stimulation in response to detection of a respiratory disorder (disordered breathing) such as apnea, hypopnea, or dyspnea. In one embodiment, the neural stimulation system delivers neural stimulation to autonomic nerves such as the vagus nerve of the parasympathetic nervous system. The stimulation of the vagus nerve is referred to as vagal nerve stimulation or vagal nerve modulation. Vagal nerve stimulation may be applied to treat heart diseases, hypertension, inflammatory disease, epilepsy, diabetes, depression, and other ailments. However, vagal nerve stimulation may also cause undesirable effects in respiration such as reduced respiratory rate and reduced tidal volume, and worsen the condition of a patient who already suffers from a respiratory disorder. Therefore, respiratory disorders such as apnea, hypopnea, and dyspnea have been contraindication for vagal nerve stimulation. In one embodiment, the neural stimulation system senses a respiratory signal indicative of respiratory cycles and synchronizes the delivery of neural stimulation to the respiratory cycles. This provides an inherent negative feedback that reduces the intensity of neural stimulation when the respiratory rate decreases. In another embodiment, the neural stimulation system detects respiratory disorders such as apnea, hypopnea, and dyspnea. If such a respiratory disorder is detected, the delivery of neural stimulation is adjusted to reduce the intensity of stimulation, suspend the stimulation, or apply a respiratory therapy using neural stimulation or other means to treat the detected respiratory disorder. In other embodiments, the neural stimulation system also delivers neural stimulation to the sympathetic system.

While vagal nerve stimulation is discussed as a specific example of neural stimulation, the present subject matter is applicable to any neural stimulation that affects respiration. While delivery of "neural stimulation pulses" to the nervous system is discussed as a specific example of neural stimulation, the present subject matter is applicable to stimulation of the nervous system using various energy forms and various signal morphologies. In one embodiment, the neural stimulation includes delivery of electrical pulses to the nervous system to artificially elicit action potentials in the nervous system. In other embodiments, the neural stimulation includes delivery of any form of energy that is capable of eliciting or modulating neural activities in the nervous system, such as electrical, mechanical, thermal, optical, chemical, and biological energies.

FIG. 1 is an illustration of an embodiment of a neural stimulation system 100 and portions of an environment in which system 100 is used. System 100 includes implantable medical device 110 that delivers neural stimulation pulses through leads 106 and 108, an external system 120, and a telemetry link 125 providing for communication between implantable medical device 110 and external system 120. For illustrative purposes only, FIG. 1 shows that lead 106 includes an electrode 107 coupled to a nerve 102 of the sympathetic nervous system, and lead 108 includes an electrode 109 coupled a nerve 104 of the parasympathetic nervous system. Nerves 102 and 104 innervate a heart 101. In various embodiments, implantable medical device 110 provides neural stimulation to any one or more nerves through one or more leads for modulating one or more functions of the circulatory system including heart 101. Such leads include implantable neural leads each including at least one electrode for sensing neural activities and/or delivering neural stimulation pulses. One example of such an electrode includes a cuff electrode for placement around the vagus nerve.

Implantable medical device 110 delivers the neural stimulation pulses and includes a respiration-controlled neural stimulation circuit 130. Respiration-controlled neural stimulation circuit 130 controls the delivery of neural stimulation pulses using indications of respiratory cycles and functions extracted from a respiratory signal. In one embodiment, respiration-controlled neural stimulation circuit 130 detects a predetermined type respiratory fiducial point from each respiratory cycle and synchronizes the delivery of neural stimulation pulses to that respiratory fiducial point. In another embodiment, respiration-controlled neural stimulation circuit 130 detects predetermined type respiratory disorders and suspends or adjusts the delivery of neural stimulation pulses upon detection of a respiratory disorder. In one embodiment, implantable medical device 110 is capable of monitoring physiologic signals and/or delivering therapies in addition to the neural stimulation. Examples of such additional therapies include cardiac pacing therapy, cardioversion/defibrillation therapy, cardiac resynchronization therapy, cardiac remodeling control therapy, drug therapy, cell therapy, and gene therapy. In various embodiments, implantable medical device 110 delivers the neural stimulation in coordination with one or more such additional therapies.

External system 120 provides for control of and communication with implantable medical device 110 by a physician or other caregiver. In one embodiment, external system 120 includes a programmer. In another embodiment, external system 120 is a patient management system including an external device communicating with implantable medical device 110 via telemetry link 125, a remote device in a remote location, and a telecommunication network linking the external device and the remote device. The patient management system allows access to implantable medical device 110 from the remote location, for purposes such as monitoring patient status and adjusting therapies. In one embodiment, telemetry link 125 is an inductive telemetry link. In an alternative embodiment, telemetry link 125 is a far-field radio-frequency (RF) telemetry link. Telemetry link 125 provides for data transmission from implantable medical device 110 to external system 120. This includes, for example, transmitting real-time physiologic data acquired by implantable medical device 110, extracting physiologic data acquired by and stored in implantable medical device 110, extracting patient history data such as occurrences of arrhythmias and therapy deliveries recorded in implantable medical device 110, and/or extracting data indicating an operational status of implantable medical device 110 (e.g., battery status and lead impedance). Telemetry link 125 also provides for data transmission from external system 120 to implantable medical device 110. This includes, for example, programming implantable medical device 110 to acquire physiologic data, programming implantable medical device 110 to perform at least one self-diagnostic test (such as for a device operational status), programming implantable medical device 110 to deliver one or more therapies and/or to adjust the delivery of one or more therapies, and/or transmitting externally acquired physiologic and/or other patient data for used by implantable medical device 110 to control the one or more therapies.

Figure 2:
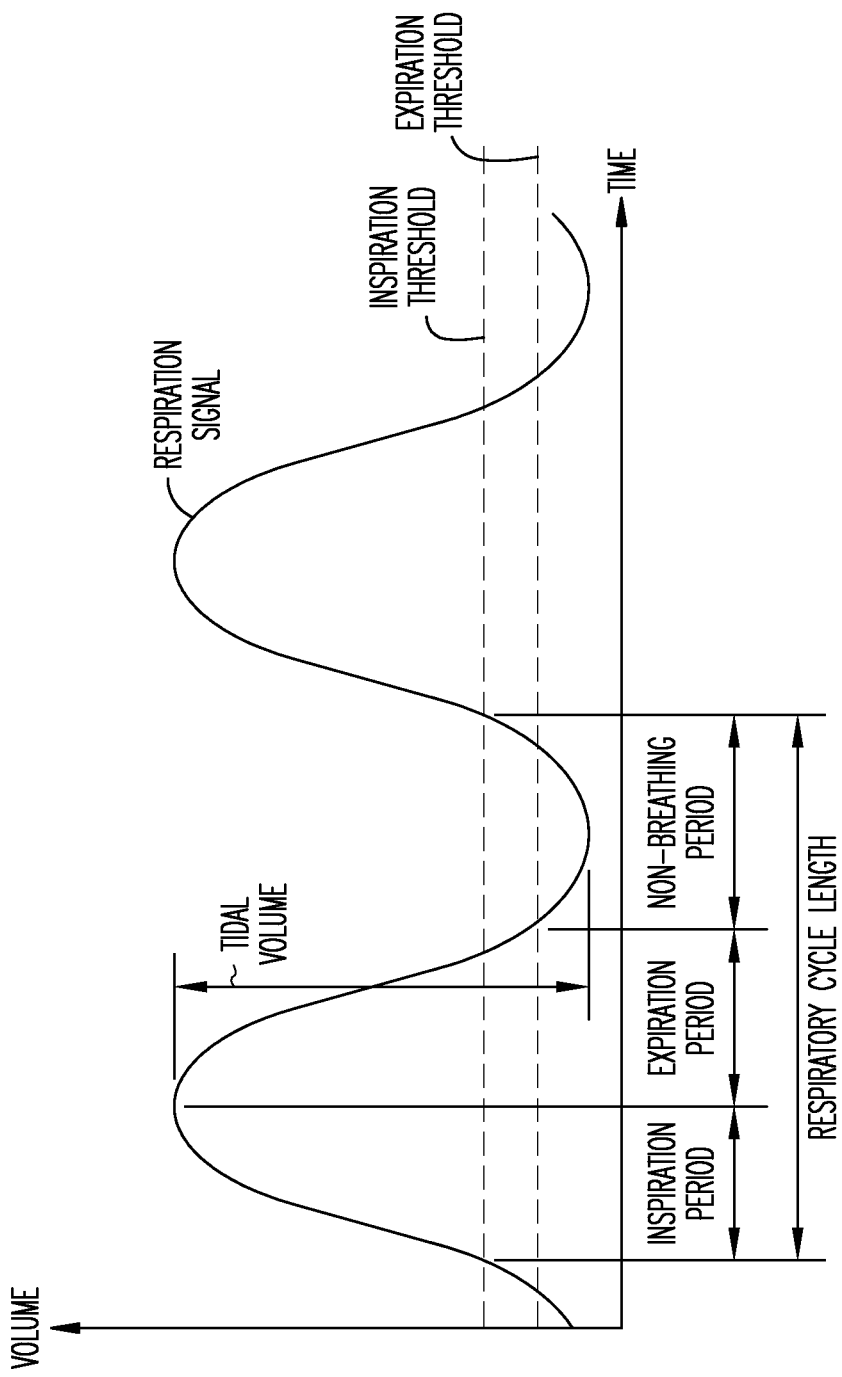
FIG. 2 is an illustration of a respiratory signal indicative of respiratory cycles and respiratory parameters.

FIG. 2 is an illustration of a respiratory signal indicative of respiratory cycles and respiratory parameters including respiratory cycle length, inspiration period, expiration period, non-breathing period, and tidal volume. The inspiration period starts at the onset of the inspiration phase of a respiratory cycle, when the amplitude of the respiratory signal rises above an inspiration threshold, and ends at the onset of the expiration phase of the respiratory cycle, when the amplitude of the respiratory cycle peaks. The expiration period starts at the onset of the expiration phase and ends when the amplitude of the respiratory signal falls below an expiration threshold. The non-breathing period is the time interval between the end of the expiration phase and the beginning of the next inspiration phase. The tidal volume is the peak-to-peak amplitude of the respiratory signal.

The respiratory signal is a physiologic signal indicative of respiratory activities. In various embodiments, the respiratory signal includes any physiology signal that is modulated by respiration. In one embodiment, the respiratory signal is a transthoracic impedance signal sensed by an implantable impedance sensor. In another embodiment, the respiratory signal is extracted from a blood pressure signal that is sensed by an implantable pressure sensor and includes a respiratory component. In another embodiment, the respiratory signal is sensed by an external sensor that senses a signal indicative of chest movement or lung volume.

Figure 3:
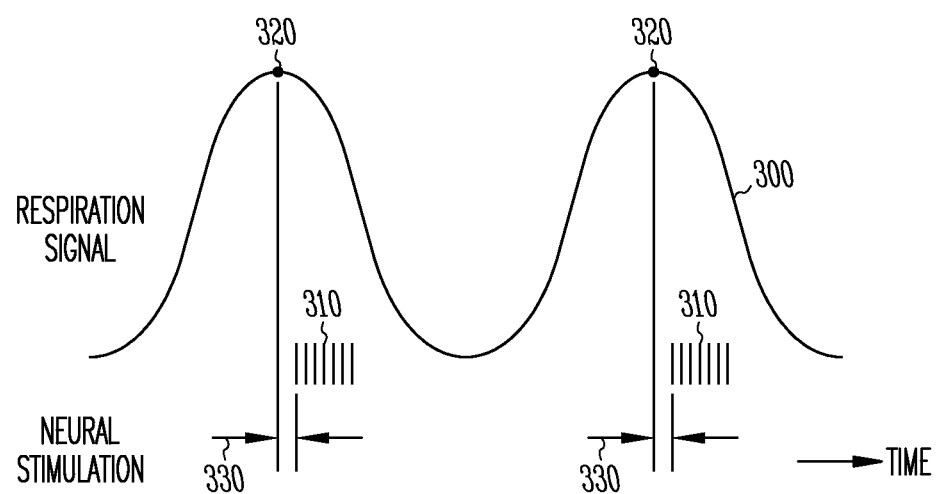
FIG. 3 is an illustration of a delivery of neural stimulation pulses synchronized to respiratory cycles.

FIG. 3 is an illustration of a delivery of neural stimulation pulses synchronized to respiratory cycles. In the illustrated embodiment, peaks 320 of a respiratory signal 300 are detected as the respiratory fiducial points. A delay interval 330 starts upon the detection of each of peaks 320. A burst of neural stimulation pulses 310 is delivered to a nerve such as the vagus nerve when delay interval 330 expires. In various other embodiments, onset points of the inspiration phases, ending points of the expiration phases, or other threshold-crossing points are detected as the respiratory fiducial points.

Figure 4:
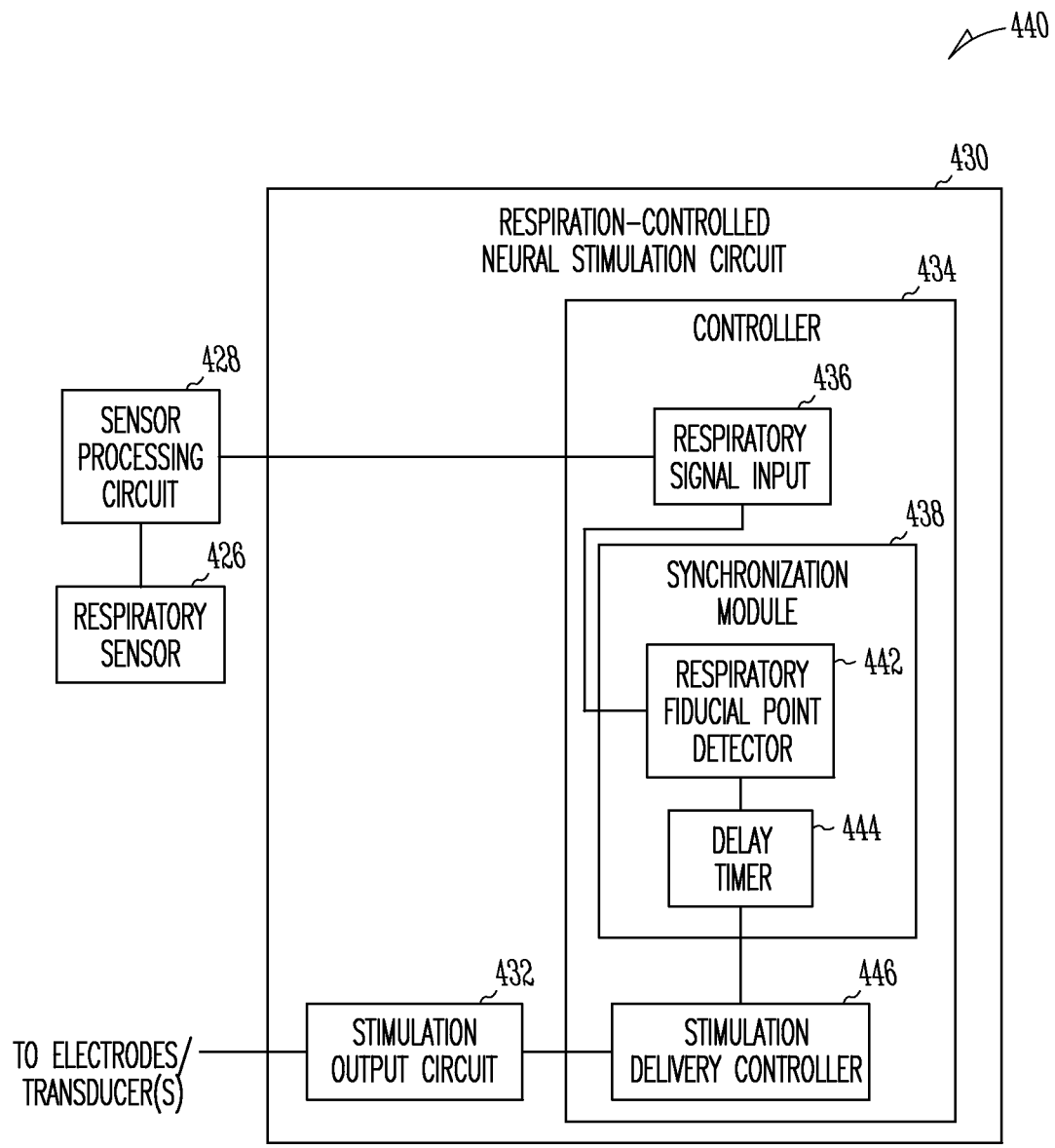
FIG. 4 is a block diagram illustrating an embodiment of a respiratory cycle-synchronized neural stimulation system.

FIG. 4 is a block diagram illustrating an embodiment of a respiratory cycle-synchronized neural stimulation system 440. System 440 includes a respiratory sensor 426, a sensor processing circuit 428, and respiration-controlled neural stimulation circuit 430.

Respiratory sensor 426 senses a physiologic signal indicative of the respiratory cycles and the respiratory parameters. In one embodiment, respiratory sensor 426 includes an implantable sensor incorporated into implantable medical device 110. In a specific embodiment, respiratory sensor 426 is an impedance sensor that senses a transthoracic impedance signal indicative of respiration. In another embodiment, respiratory sensor 426 includes an implantable sensor or a portion thereof. The implantable sensor is communicatively coupled to the implantable medical device via one or more leads or via telemetry. In a specific embodiment, respiratory sensor 426 is an implantable pulmonary artery pressure (PAP) sensor or a portion thereof. The implantable PAP sensor communicates with implantable medical device 100 via RF or ultrasonic telemetry. An example of the implantable PAP sensor is discussed in U.S. patent application Ser. No. 11/249,624, entitled "METHOD AND APPARATUS FOR PULMONARY ARTERY PRESSURE SIGNAL ISOLATION", filed on Oct. 13, 2005, now issued as U.S. Pat. No. 7,566,308, assigned to Cardiac Pacemakers, Inc., which is incorporated by reference herein in its entirety. In another embodiment, respiratory sensor 426 includes an external sensor that senses the expansion and contraction of the chest or a portion thereof. The external sensor communicates with implantable medical device 100 via RF or ultrasonic telemetry.

Sensor processing circuit 428 produces the respiratory signal using the physiologic signal. The respiratory signal is indicative of respiratory cycles and respiratory parameters including one or more of respiratory cycle length, inspiration period, expiration period, non-breathing period, tidal volume, and minute ventilation. In one embodiment, sensor processing circuit 428 removes unwanted components of the physiologic signal to isolate the respiratory components of the physiologic signal. One example includes isolating the respiratory components of a PAP signal, which is discussed in U.S. patent application Ser. No. 11/249,624, now issued as U.S. Pat. No. 7,566,308. In one embodiment, sensor processing circuit 428 extracts one or more of the respiratory parameters. In one embodiment, sensor processing circuit 428 and respiration-controlled neural stimulation circuit 430 are both housed in implantable medical device 110. In another embodiment, sensor processing circuit 428 is part of an implantable or external sensor that includes respiratory sensor 426.

Respiration-controlled neural stimulation circuit 430 is a specific embodiment of respiration-controlled neural stimulation circuit 130 and includes a stimulation output circuit 432 and a controller 434. Stimulation output circuit 432 delivers neural stimulation pulses via electrodes such as electrodes 107 and 109. Controller 434 includes a respiratory signal input 436, a synchronization module 438, and a stimulation delivery controller 446. Respiratory signal input 436 receives the respiratory signal indicative of respiratory cycles and respiratory parameters. Synchronization module 438 synchronizes the delivery of the neural stimulation pulses to the respiratory cycles and includes a respiratory fiducial point detector 442 and a delay timer 444. Respiratory fiducial point detector 442 detects predetermined-type respiratory fiducial points in the respiratory signal. Delay timer 444 times a delay interval starting with each of the detected respiratory fiducial points. Stimulation delivery controller 446 causes stimulation output circuit 432 to deliver a burst of the neural stimulation pulses when the delay interval expires.

Figure 5:
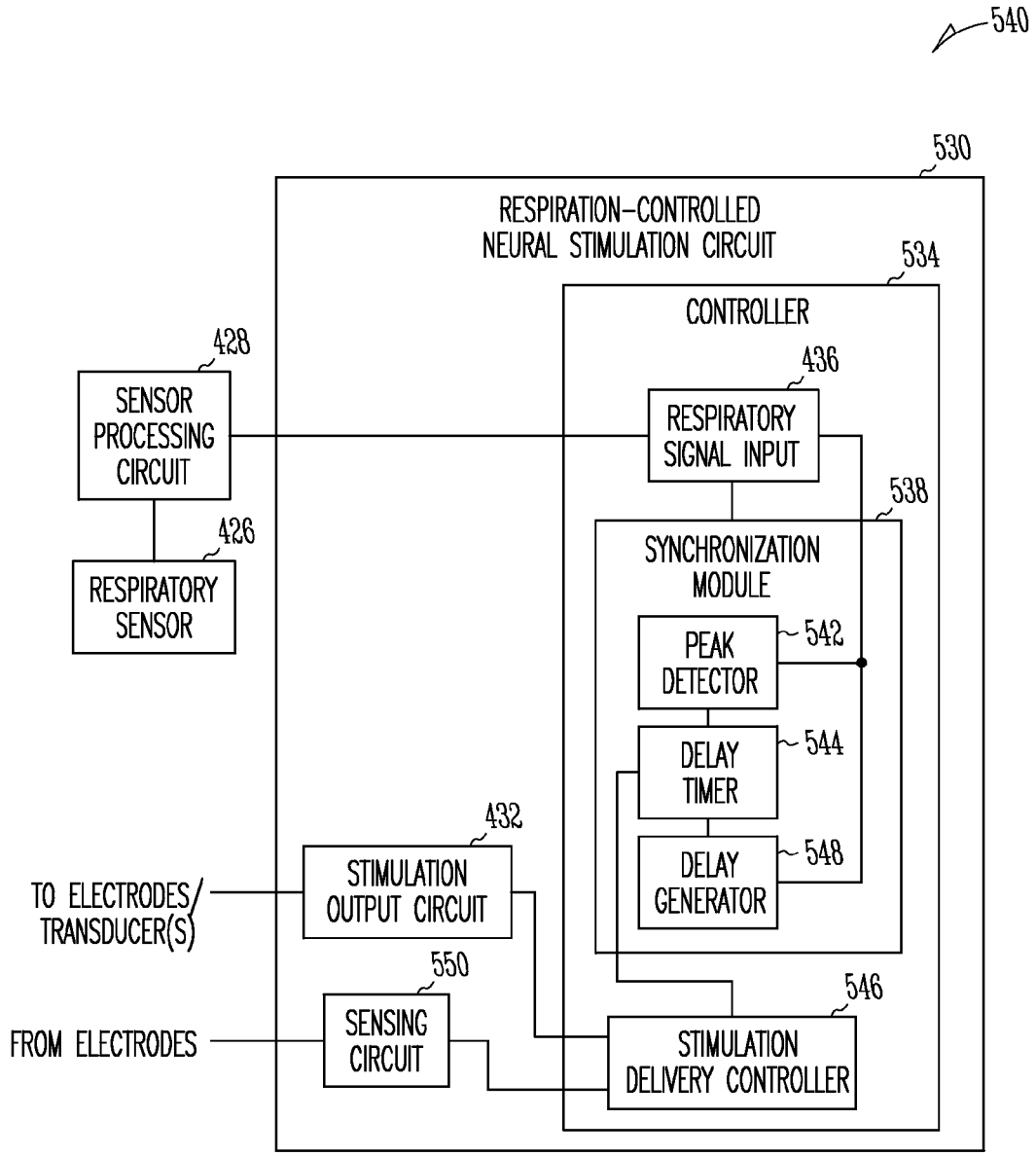
FIG. 5 is a block diagram illustrating a specific embodiment of the respiratory cycle-synchronized neural stimulation system of FIG. 4.

FIG. 5 is a block diagram illustrating an embodiment of a respiratory cycle-synchronized neural stimulation system 540, which is a specific embodiment of respiratory cycle-synchronized neural stimulation system 440. System 540 includes respiratory sensor 426, sensor processing circuit 428, and a respiration-controlled neural stimulation circuit 530.

Respiration-controlled neural stimulation circuit 530 is a specific embodiment of respiration-controlled neural stimulation circuit 430 and includes stimulation output circuit 432, a sensing circuit 550, and a controller 534. Sensing circuit 550 senses one or more neural signals using electrodes such as electrodes 107 and 109. Controller 534 includes respiratory signal input 436, a synchronization module 538, and a stimulation delivery controller 546. Synchronization module 538 synchronizes the delivery of the neural stimulation pulses to the respiratory cycles. Such synchronization between respiratory cycles and neural stimulation provides a negative feedback to mitigate undesirable effects such as abnormally long respiratory cycle lengths caused by the neural stimulation. In one embodiment, the synchronization between respiratory cycles and neural stimulation allows the neural stimulation to mimic the natural heart rate modulation by the respiration where the heart rate increases during the inspiration phase and decreases during the expiration phase. In a further embodiment, in addition to synchronizing neural stimulation to respiratory cycles, synchronization module 538 also synchronizes the neural stimulation to cardiac cycles and/or circadian cycles. Synchronization module 538 includes a peak detector 542, a delay timer 544, and a delay generator 548. Peak detector 542 is a specific embodiment of respiratory fiducial point detector 442 and detects high or low peaks of the respiratory signal. In one embodiment, peak detector 542 detects high peaks illustrated in FIG. 3 as peaks 320. Delay timer 544 times the delay interval that starts with the detected peaks. In one embodiment, the delay interval is programmable between approximately 0 and 5 seconds. In another embodiment, delay generator 548 adjusts the delay interval using the respiratory signal. In a specific embodiment, delay generator 548 calculates the delay interval as a function of the respiratory cycle length. Stimulation delivery controller 546 is a specific embodiment of stimulation delivery controller 446 and controls the delivery of the neural stimulation pulses by executing a stimulation algorithm including a set of stimulation parameters. In various embodiments, the stimulation parameters include pulse amplitude, pulse width, stimulation frequency or inter-pulse interval, number of pulses per burst, and stimulation sites. Stimulation delivery controller 546 causes stimulation output circuit 432 to deliver a burst of the neural stimulation pulses when the delay interval expires.

Figure 6:
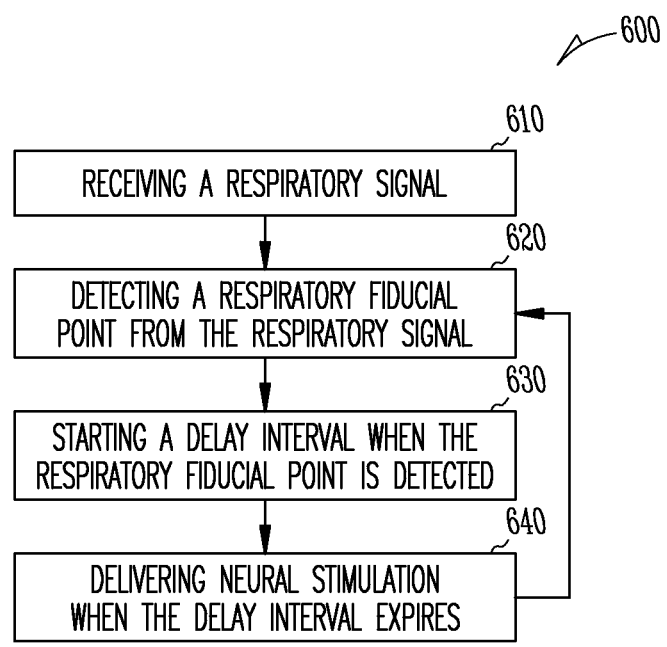
FIG. 6 is a flow chart illustrating an embodiment of a method for synchronizing neural stimulation to respiratory cycles.

FIG. 6 is a flow chart illustrating an embodiment of a method 600 for synchronizing neural stimulation to respiratory cycles. In one embodiment, method 600 is performed by respiration-controlled neural stimulation circuit 430 or 530.

A respiratory signal is received at 610. The respiratory signal is indicative of respiratory cycles and respiratory parameters. Examples of the respiratory parameters include the respiratory cycle length, the inspiration period, the expiration period, the non-breathing interval, the tidal volume, and the minute ventilation. In various embodiments, the respiratory signal is, or is derived from, a physiologic signal indicative of the respiratory cycles and the respiratory parameters. Examples of the physiologic signal include a transthoracic impedance signal and blood pressure signals such as a PAP signal.

A respiratory fiducial point is detected from the respiratory signal at 620. Examples of the respiratory fiducial point include high or low peaks of the respiratory signal and threshold-crossing points in the respiratory signal.

A delay interval is started at 630, when the respiratory fiducial point is detected. In one embodiment, the delay interval is programmable between approximately 0 and 5 seconds. In another embodiment, the delay interval is adjusted using the respiratory signal. In a specific embodiment, the delay interval is calculated as a function of the respiratory cycle length and/or one or more other respiratory parameters extracted from the respiratory signal.

A burst of neural stimulation pulses is delivered when the delay interval expires at 640. In various embodiments, the delivery of the neural stimulation pulses is controlled by executing a stimulation algorithm including a set of stimulation parameters such as one or more of pulse amplitude, pulse width, stimulation frequency or inter-pulse interval, number of pulses per burst, and stimulation sites.

Figure 7:
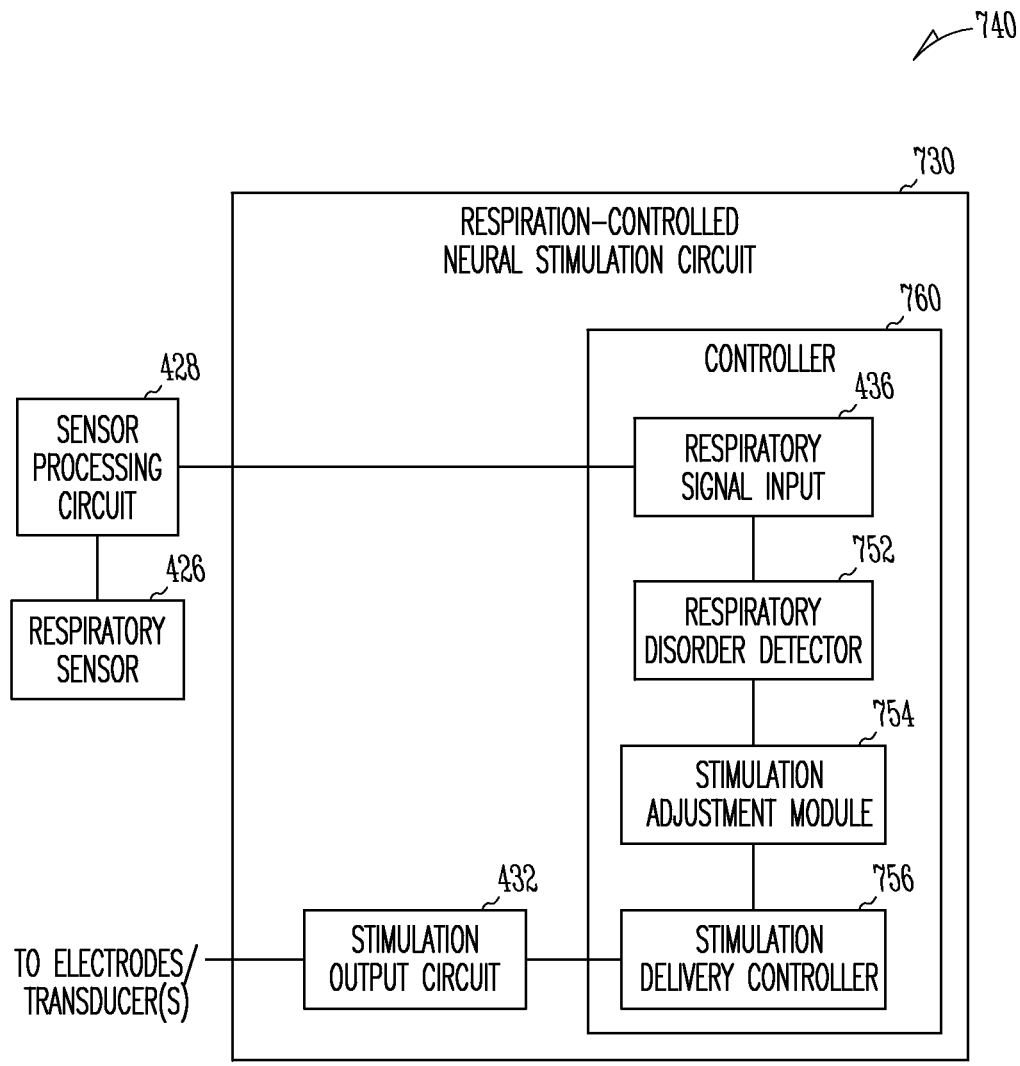
FIG. 7 is a block diagram illustrating an embodiment of a respiratory disorder-responsive neural stimulation system.

FIG. 7 is a block diagram illustrating an embodiment of a respiratory disorder-responsive neural stimulation system 740. System 740 includes respiratory sensor 426, sensor processing circuit 428, and a respiration-controlled neural stimulation circuit 730.

Respiration-controlled neural stimulation circuit 730 is a specific embodiment of respiration-controlled neural stimulation circuit 130 and includes stimulation output circuit 432 and a controller 760. Controller 760 includes respiratory signal input 436, a respiratory disorder detector 752, a stimulation adjustment module 754, and a stimulation delivery controller 756. Respiratory disorder detector 752 detects predetermined-type respiratory disorders using the respiratory signal received by respiratory signal input 436. Stimulation adjustment module 754 adjusts the delivery of the neural stimulation pulses in response to the detection of each of the respiratory disorders. In one embodiment, stimulation adjustment module 754 stops the execution of a stimulation algorithm in response to the detection of a respiratory disorder. Stimulation delivery controller 756 controls the delivery of the neural stimulation pulses by executing one or more stimulation algorithms.

Figure 8:
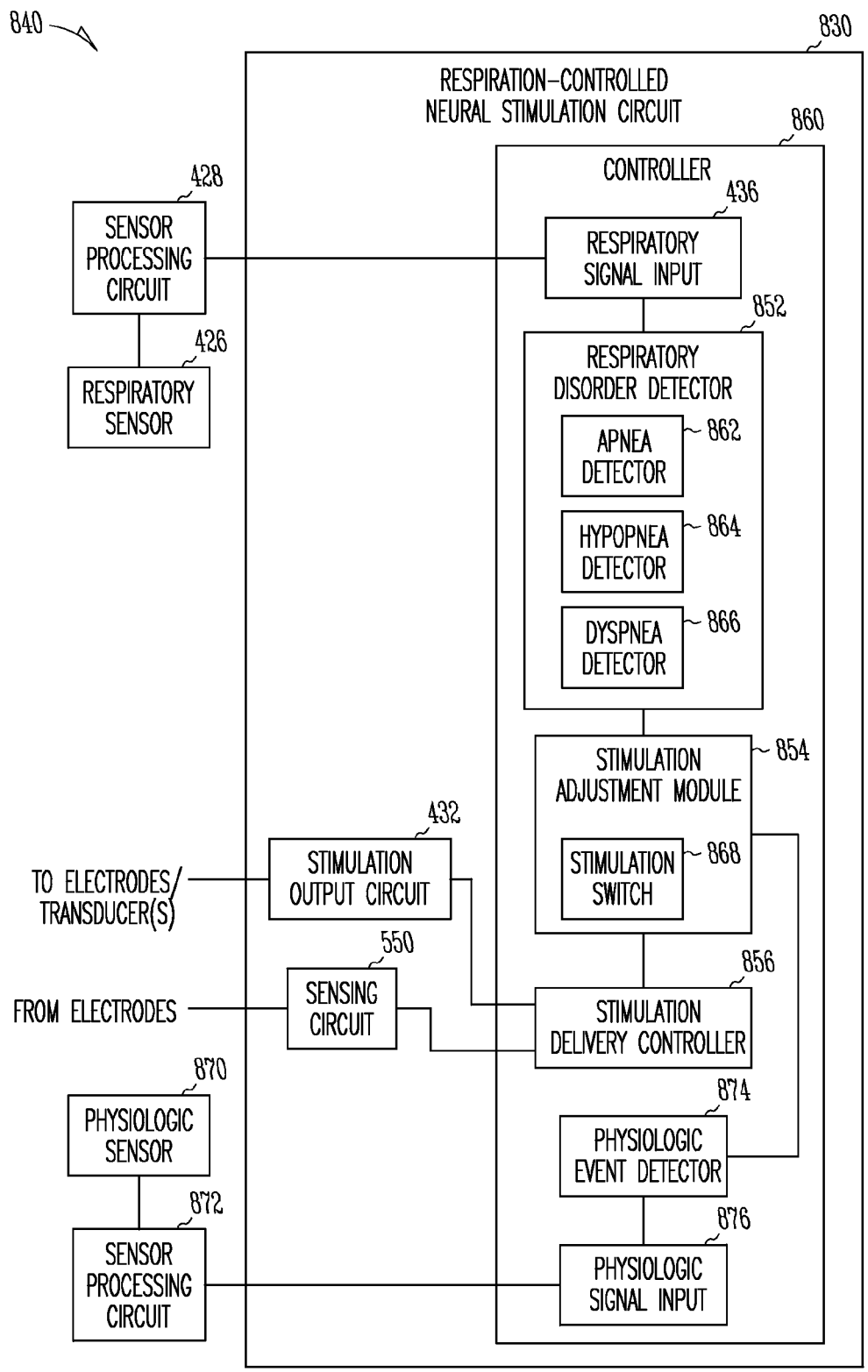
FIG. 8 is a block diagram illustrating a specific embodiment of the respiratory disorder-responsive neural stimulation system of FIG. 7.

FIG. 8 is a block diagram illustrating an embodiment of a respiratory disorder-responsive neural stimulation system 840, which is a specific embodiment of respiratory disorder-responsive neural stimulation system 740. System 840 includes respiratory sensor 426, sensor processing circuit 428, a physiologic sensor 870, another sensor processing circuit 872, and a respiration-controlled neural stimulation circuit 830.

Physiologic sensor 870 senses one or more physiologic signals in addition to the physiologic signal sensed by respiratory sensor 426 and the one or more neural signals sensed by sensing circuit 550. In various embodiments, physiologic sensor 870 senses one or more of cardiac signals, signals indicative of heart sounds, cardiac and/or transthoracic impedance signals, and signals indicative of blood oxygen level. Sensor processing circuit 872 processes the one or more physiologic signals sensed by physiologic sensor 870 for use by respiration-controlled neural stimulation circuit 830 in controlling the neural stimulation. In various embodiments, physiologic sensor 870 or portions of physiologic sensor 870 are included in implantable medical device 110 or communicatively coupled to implantable medical device 110 via one or more leads or telemetry. In various embodiments, sensor processing circuit 872 or portions sensor processing circuit 872 are included in implantable medical device 110 or communicatively coupled to implantable medical device 110 via one or more leads or telemetry.

Respiration-controlled neural stimulation circuit 830 is a specific embodiment of respiration-controlled neural stimulation circuit 130 and includes stimulation output circuit 432, sensing circuit 550, and a controller 860. Controller 860 is a specific embodiment of controller 760 and includes respiratory signal input 436, a respiratory disorder detector 852, a physiologic signal input 876, a physiologic event detector 874, a stimulation adjustment module 854, and a stimulation delivery controller 856.

Respiratory disorder detector 852 detects one or more respiratory disorders using the respiratory signal. In the illustrated embodiment, respiratory disorder detector 852 includes an apnea detector 862, a hypopnea detector 864, and a dyspnea detector 866. In various other embodiments, respiratory disorder detector 852 includes any one or more of apnea detector 862, hypopnea detector 864, and dyspnea detector 866. In various embodiments, respiratory disorder detector 852 also detects abnormal values of one or more respiratory parameters, such as a low respiratory rate when the respiratory rate is below a threshold rate, a low tidal volume when the tidal volume is below a detection threshold volume, and a low minute ventilation when the minute ventilation is below a detection threshold value.

Apnea is characterized by abnormally long non-breathing periods. Apnea detector 862 detects apnea by comparing the non-breathing period to a detection threshold period. Apnea is detected when the non-breathing period exceeds the detection threshold period. Hypopnea is characterized by abnormally shallow breathing, i.e., low tidal volume. Hypopnea detector 864 detects hypopnea by comparing the tidal volume to a detection threshold volume. Hypopnea is detected when the tidal volume is below the detection threshold volume. In one embodiment, the tidal volume is an average tidal volume over a predetermined time interval or a predetermined number of respiratory cycles. Dyspnea is characterized by rapid shallow breathing, i.e., high respiratory rate-to-tidal volume ratio. Dyspnea detector 866 detects dyspnea by comparing the ratio of the respiratory rate to the tidal volume to a detection threshold ratio. Dyspnea is detected when the ratio exceeds the threshold ratio. In various embodiments, the threshold period, the detection threshold volume, and/or the threshold ratio are empirically established. An example of apnea and hypopnea detection using a respiratory signal such as a transthoracic impedance signal is discussed in U.S. patent application Ser. No. 10/309,770, now issued as U.S. Pat. No. 7,252,640, entitled "DETECTION OF DISORDERED BREATHING," filed on Dec. 4, 2002, assigned to Cardiac Pacemakers, Inc., which is incorporated by reference herein in its entirety. An example of dyspnea detection using a respiratory signal such as a transthoracic impedance signal is discussed in U.S. patent application Ser. No. 11/229,316, entitled "RAPID SHALLOW BREATHING DETECTION FOR USE IN CONGESTIVE HEART FAILURE STATUS DETERMINATION," filed on Sep. 16, 2005, now issued as U.S. Pat. No. 7,775,983, assigned to Cardiac Pacemakers, Inc., which is incorporated by reference herein in its entirety.

Physiologic signal input 876 receives the one or more physiologic signals sensed by physiologic sensor 870 and processed by sensor processing circuit 872. Physiologic event detector 874 detects one or more physiologic events from the one or more physiologic signals. In various embodiments, physiologic event detector 874 detects one or more of changes in cardiac signal morphology, changes in heart sound waveform morphology, changes in impedance signal morphology, and changes in blood oxygen saturation.

Stimulation adjustment module 854 adjusts the delivery of the neural stimulation pulses in response to at least the detection of a respiratory disorder by respiratory disorder detector 852. In one embodiment, stimulation adjustment module 854 adjusts the delivery of the neural stimulation pulses in response to the detection of a respiratory disorder by respiratory disorder detector 852 and the detection of a physiologic event by physiologic event detector 874. Stimulation delivery controller 856 controls the delivery of the neural stimulation pulses by executing one or more stimulation algorithms. Stimulation adjustment module 854 includes a stimulation switch 868. Stimulation switch 868 stops executing a first stimulation algorithm in response to the detection of a respiratory disorder such as apnea, hypopnea, or dyspnea. For example, the first stimulation algorithm is executed to treat a cardiac condition by vagal nerve stimulation. If apnea, hypopnea, or dyspnea is detected, the vagal nerve stimulation is to be stopped to avoid the worsening of the condition due to the vagal nerve stimulation designed for treating the cardiac condition. In one embodiment, stimulation switch 868 resumes the execution of the first stimulation algorithm after a predetermined suspension period. In another embodiment, stimulation switch 868 resumes the execution of the first stimulation algorithm when the respiratory disorder is no longer detected. In another embodiment, stimulation switch 868 resumes the execution of the first stimulation algorithm after a predetermined suspension period. In another embodiment, stimulation switch 868 resumes the execution of the first stimulation algorithm in response to a stimulation command issued by a user such as a physician using external system 120. In one embodiment, in addition to stopping the execution of the first stimulation algorithm, stimulation switch 868 starts executing a second stimulation algorithm in response to the detection of the respiratory disorder. In a specific embodiment, the second stimulation algorithm provides lower stimulation intensity when compared to the first stimulation algorithm. Switching from the first stimulation algorithm to the second stimulation algorithm lowers the stimulation pulse amplitude, shortens stimulation pulse width, lowers the stimulation frequency, reduces the number of pulses per burst, and/or changes stimulation sites. In another specific embodiment, the first stimulation algorithm is used to treat a non-respiratory disorder such as a cardiac disorder, and the second stimulation algorithm is used to treat the detected respiratory disorder, such as apnea, hypopnea, and dyspnea. Switching from the first stimulation algorithm to the second stimulation algorithm switches the treatment for the non-respiratory disorder to the treatment for the respiratory disorder. In another specific embodiment, the first stimulation algorithm is used to treat the non-respiratory disorder, and the second stimulation algorithm is used to treat the detected respiratory disorder in addition to treating the non-respiratory disorder. Switching from the first stimulation algorithm to the second stimulation algorithm switches the treatment for the non-respiratory disorder to the treatment for both the respiratory disorder and the non-respiratory disorder.

In one embodiment, the "respiratory disorder" discussed in this document refers to a respiratory disorder associated with sleep (i.e., sleep disordered breathing, such as sleep apnea, sleep hypopnea, or sleep dyspnea). The one or more physiologic signals indicate whether a patient is sleeping. For example, physiologic sensor 870 includes an activity sensor, a posture sensor, and/or one or more other sensors that senses a signal being a factor indicating sleeping. Physiologic event detector 874 detects sleeping based on the one or more physiologic signals and produces a sleeping signal indicating whether the patient is sleeping. In one embodiment, physiologic event detector 874 detects sleeping based on the one or more physiologic signals and the time of the day. Respiratory disorder detector 852 detects such one or more respiratory disorders when the sleeping signal is present. Stimulation adjustment module 854 adjusts the delivery of the neural stimulation pulses in response to at least one respiratory disorder detected during sleep. In other embodiments, the "respiratory disorder" discussed in this document includes a respiratory disorder that occurs while the patient is awake or sleep.

In one embodiment, the "respiratory disorder" discussed in this document refers to a respiratory disorder induced by neural stimulation. A patient may have one or more respiratory disorders that are unrelated to the vagal nerve stimulation. The respiratory disorder induced by neural stimulation includes a respiratory disorder that is caused or worsened by the vagal nerve stimulation. In one embodiment, the one or more physiologic signals sensed by physiologic sensor 870 indicate whether a respiratory disorder is induced by the vagal nerve stimulation. For example, because speech may interfere with the detection of the one or more respiratory disorders, physiologic sensor 870 includes an accelerometer or microphone to detect a signal indicative of speech. Physiologic event detector 874 detects speech using the signal and produces a speech signal indicating whether the patient is talking Respiratory disorder detector 852 detects one or more respiratory disorders when the speech signal is not present. In another example, respiratory disorder detector 852 detects the one or more respiratory disorders using the respiratory signal sensed during the vagal nerve stimulation and stored baseline respiratory parameters. The baseline respiratory parameters are produced from the respiratory signal sensed while the vagal nerve stimulation is not delivered. Respiratory disorder detector 852 uses the baseline respiratory parameters to isolate the effect of the vagal nerve stimulation in the respiratory signal for the detection of the one or more respiratory disorders. In various embodiments, respiratory disorder detector 852 detects one or more respiratory disorders induced by vagal nerve stimulation using the respiratory signal and other signals such as a signal indicative of whether the vagal nerve stimulation is being delivered, a signal indicative of time of the day, and one or more physiologic signals allowing for determination of whether a respiratory disorder is caused or worsened by the vagal nerve stimulation. Stimulation adjustment module 854 adjusts the delivery of the neural stimulation pulses in response to at least one respiratory disorder induced by the delivery of the neural stimulation pulses.

Figure 9:
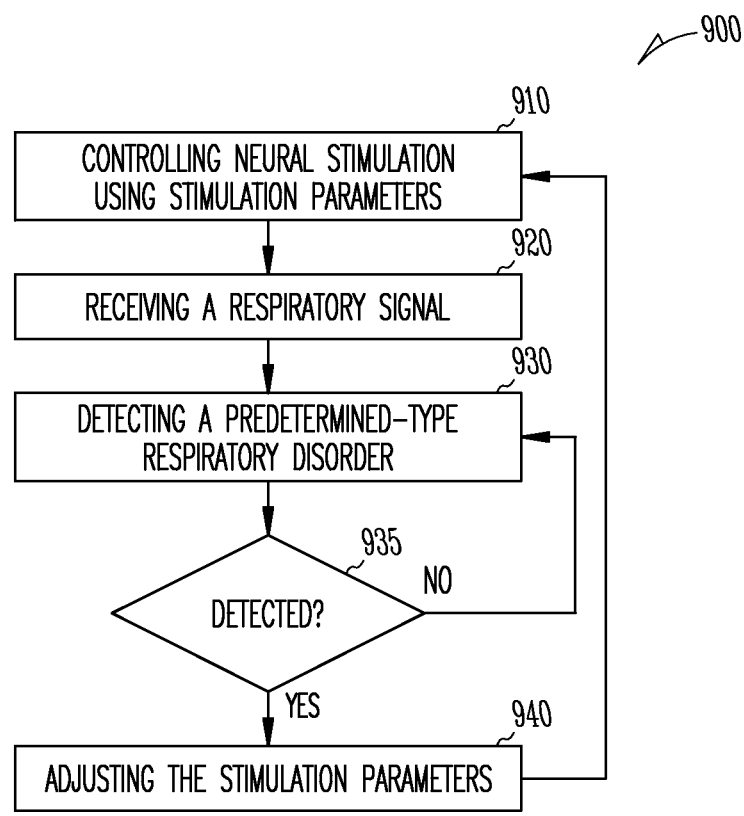
FIG. 9 is a flow chart illustrating an embodiment of a method for adjusting neural stimulation in response to a respiratory disorder.

FIG. 9 is a flow chart illustrating an embodiment of a method 900 for adjusting neural stimulation in response to a respiratory disorder. In one embodiment, method 900 is performed by respiration-controlled neural stimulation circuit 730 or 830.

The neural stimulation is controlled by using a plurality of stimulation parameters at 910. The neural stimulation is delivered to treat a non-respiratory disorder. In one embodiment, neural stimulation is delivered to treat a cardiac condition, such as to treat heart failure or to control cardiac remodeling.

A respiratory signal is received at 920. The respiratory signal is indicative of respiratory cycles and respiratory parameters. Examples of the respiratory parameters include the respiratory cycle length, the inspiration period, the expiration period, the non-breathing period, the tidal volume, and the minute ventilation. In various embodiments, the respiratory signal is, or is derived from, a physiologic signal indicative of the respiratory cycles and the respiratory parameters. Examples of the physiologic signal include a transthoracic impedance signal and blood pressure signals such as a PAP signal.

A respiratory disorder is being detected at 930. Examples of the respiratory disorder include abnormal respiratory parameter values such as low respiratory rate, low tidal volume, and low minute ventilation, apnea, hypopnea, and dyspnea. Apnea is detected when the non-breathing period exceeds a detection threshold period. Hypopnea is detected when the tidal volume is below a detection threshold volume. Dyspnea is detected when the ratio of the respiratory rate to the tidal volume exceeds a detection threshold ratio.

If the respiratory disorder is detected at 935, the neural stimulation is adjusted by adjusting one or more of the stimulation parameters at 940. The neural stimulation is adjusted to terminate or mitigate the detected respiratory disorder. In one embodiment, the neural stimulation is adjusted to decrease the intensity of the stimulation. In another embodiment, the neural stimulation is suspended for a predetermined period of time or until the respiratory disorder is no longer detected. In another embodiment, the neural stimulation is adjusted to treat the detected respiratory disorder.

Figure 10:
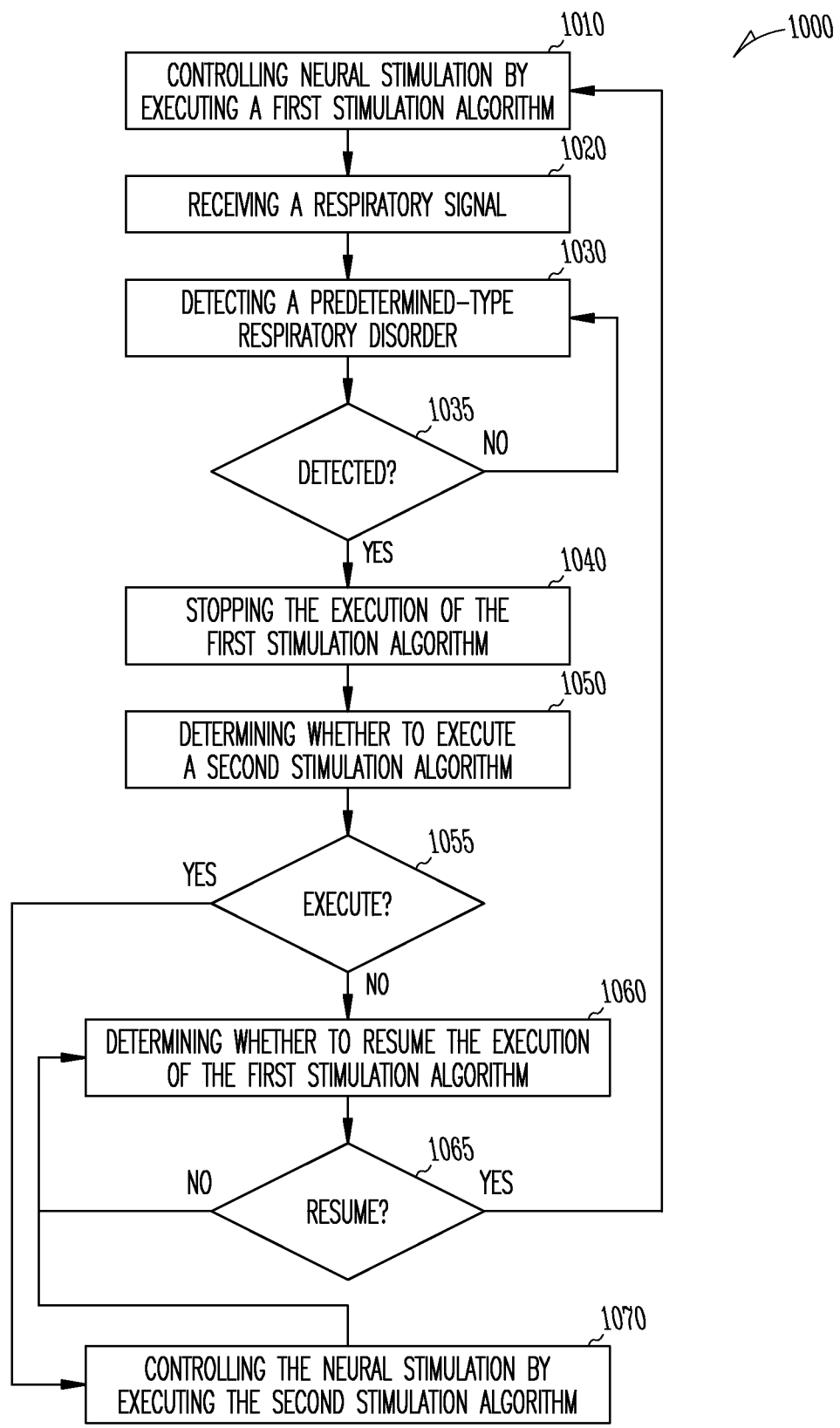
FIG. 10 is a flow chart illustrating a specific embodiment of the method for adjusting neural stimulation in response to a respiratory disorder.

FIG. 10 is a flow chart illustrating an embodiment of a method 1000 for adjusting neural stimulation in response to the detection of a respiratory disorder. Method 1000 is a specific embodiment of method 900. In one embodiment, method 1000 is performed by respiration-controlled neural stimulation circuit 730 or 830.

The neural stimulation is controlled by executing a first stimulation algorithm at 1010. In one embodiment, the first stimulation algorithm is designed to treat a cardiac condition, such as heart failure.

A respiratory signal is received at 1020. The respiratory signal is indicative of respiratory cycles and respiratory parameters. Examples of the respiratory parameters include the respiratory cycle length, the inspiration period, the expiration period, the non-breathing period, the tidal volume, and the minute ventilation. In various embodiments, the respiratory signal is, or is derived from, a physiologic signal indicative of the respiratory cycles and the respiratory parameters. Examples of the physiologic signal include a transthoracic impedance signal and blood pressure signals such as a PAP signal.

A respiratory disorder is being detected at 1030. Examples of the respiratory disorder include abnormal respiratory parameter values such as low respiratory rate, low tidal volume, and low minute ventilation, apnea, hypopnea, and dyspnea. Apnea is detected when the non-breathing period exceeds a detection threshold period. Hypopnea is detected when the tidal volume is below a detection threshold volume. Dyspnea is detected when the ratio of the respiratory rate to the tidal volume exceeds a detection threshold ratio.

If the respiratory disorder is detected at 1035, the execution of the first stimulation algorithm is stopped at 1040. Whether to execute a second stimulation algorithm is determined at 1050. If the second stimulation algorithm is determined to be executed at 1055, the neural stimulation is controlled by executing the second stimulation algorithm at 1070. In one embodiment, the second stimulation algorithm is selected to lower the stimulation intensity provided by the first stimulation algorithm. In another embodiment, the second stimulation algorithm is selected to treat the detected respiratory disorder, such as apnea, hypopnea, or dyspnea.

If the second stimulation algorithm is determined not to be executed at 1055, whether to resume the execution of the first stimulation algorithm is determined at 1060. During or after the execution of the second stimulation algorithm, whether to resume the execution of the first stimulation algorithm is also determined at 1060. If the execution of the first stimulation algorithm is resumed at 1065, the neural stimulation is again controlled by executing a first stimulation algorithm at 1010. In one embodiment, the execution the first stimulation algorithm is to be resumed after a predetermined suspension period. In another embodiment, the execution the first stimulation algorithm is to be resumed when the respiratory disorder is no longer detected. In another embodiment, the execution the first stimulation algorithm is to be resumed in response to a stimulation command issued by a user such as a physician.

In one embodiment, in addition to the response to the detection of the respiratory disorder, the delivery of the neural stimulation pulses is adjusted in response to the detection of a physiologic event. Examples of such a physiologic event include changes in cardiac signal morphology, changes in heart sound waveform morphology, changes in impedance signal morphology, and changes in blood oxygen saturation.

Figure 11:
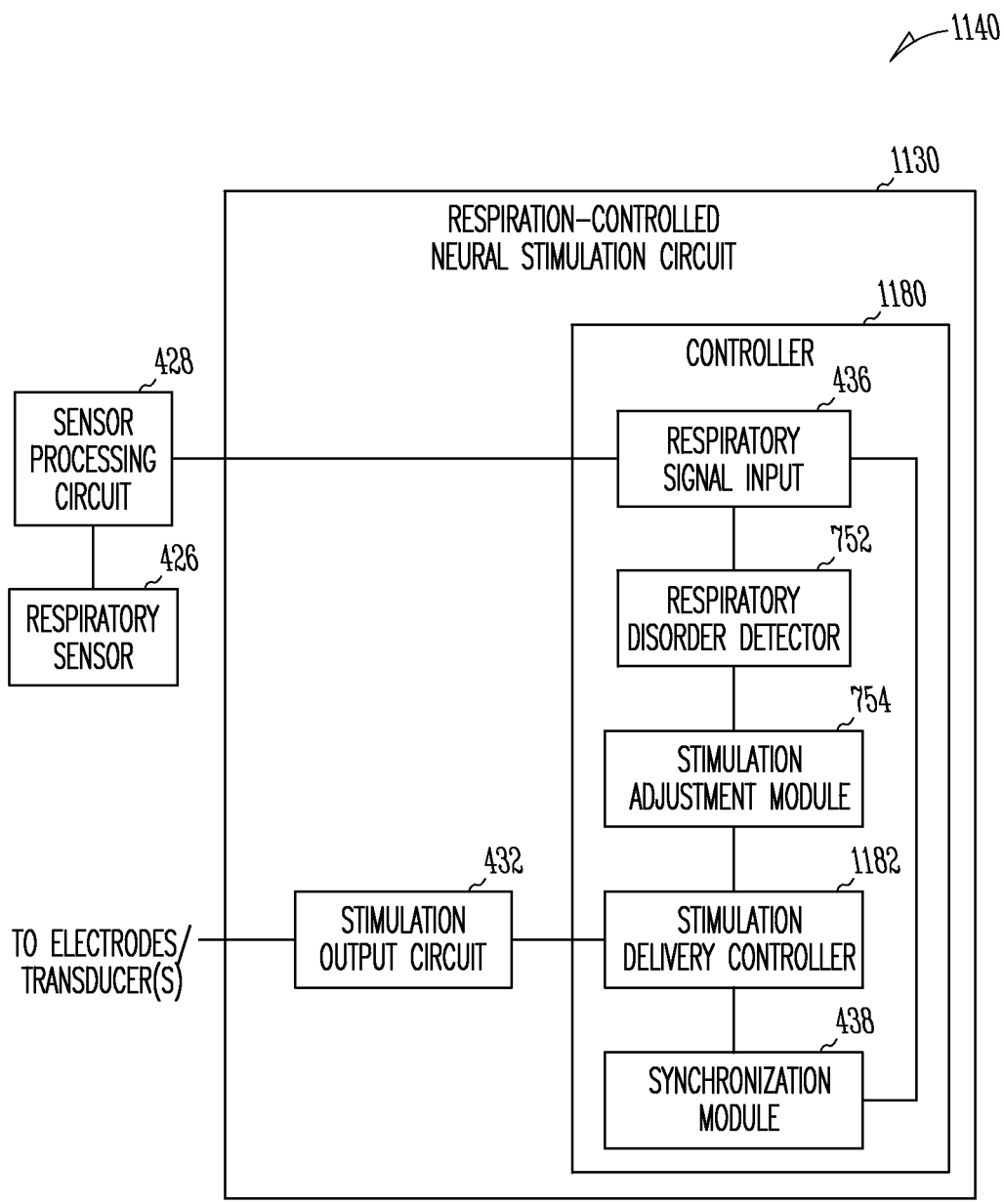
FIG. 11 is a block diagram illustrating an embodiment of a respiratory cycle-synchronized respiratory disorder-responsive neural stimulation system.

FIG. 11 is a block diagram illustrating an embodiment of a respiratory cycle-synchronized respiratory disorder-responsive neural stimulation system 1140. System 1140 represents a combination of systems 440 or 540 and systems 740 or 840. In the illustrated embodiment, system 1140 includes respiratory sensor 426, sensor processing circuit 428, and a respiration-controlled neural stimulation circuit 1130. In various specific embodiments, system 1140 may include any combination of components of systems 440, 540, 740, and 840 as discussed above.

Respiration-controlled neural stimulation circuit 1130 is a specific embodiment of respiration-controlled neural stimulation circuit 130 and includes stimulation output circuit 432 and a controller 1180. Controller 1180 includes respiratory signal input 436, respiratory disorder detector 752, stimulation adjustment module 754, synchronization module 438, and stimulation delivery controller 1182. Stimulation delivery controller 1182 controls the delivery of the neural stimulation pulses from stimulation output circuit 432 by synchronizing the delivery to the respiratory cycles, as controlled by synchronization module 438, and by responding to the detection of each respiratory disorder, as controlled by stimulation adjustment module 754.

Figure 12:
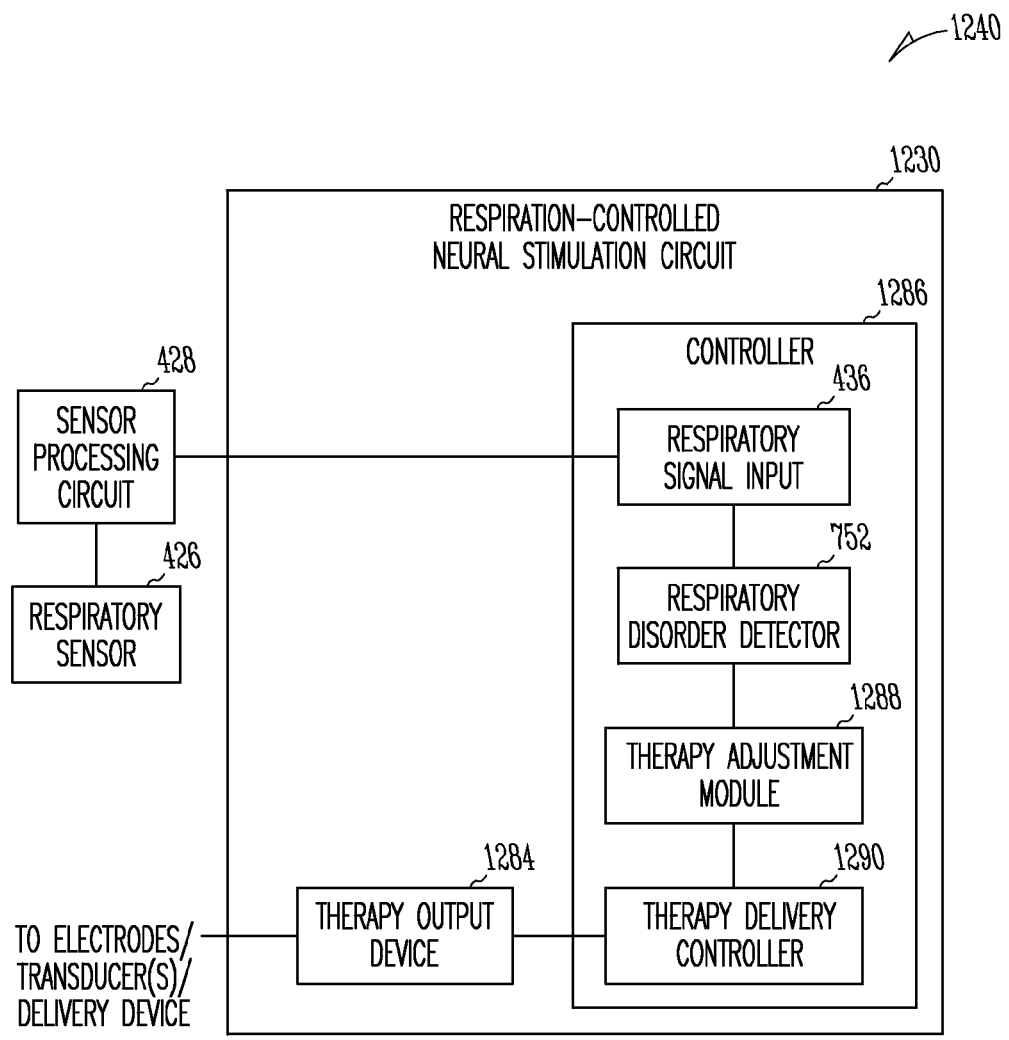
FIG. 12 is a block diagram illustrating an embodiment of another respiratory disorder-responsive neural stimulation system.

FIG. 12 is a block diagram illustrating an embodiment of a respiratory disorder-responsive neural stimulation system 1240. System 1240 includes respiratory sensor 426, sensor processing circuit 428, and a respiration-controlled neural stimulation circuit 1230.

Respiration-controlled neural stimulation circuit 1230 is another specific embodiment of respiration-controlled neural stimulation circuit 130 and includes a therapy output device 1284 and a controller 1286. Therapy output device 1284 delivers one or more therapies including a neural stimulation therapy treating a non-respiratory disorder. Controller 1286 includes respiratory signal input 436, respiratory disorder detector 752, a therapy adjustment module 1288, and a therapy delivery controller 1290. Therapy adjustment module 1288 adjusts delivery of the one or more therapies in response to the detection of a respiratory disorder by respiratory disorder detector 752. Therapy delivery controller 1290 controls the delivery of the one or more therapies using parameters set and adjusted by therapy adjustment module 1288.

In one embodiment, system 1240 provides for one or more neural stimulation therapies that include at least one neural stimulation therapy treating a non-respiratory disorder. When the respiratory disorder is detected, system 1240 starts a neural stimulation therapy treating the detected respiratory disorder and/or adjusts the neural stimulation therapy treating the non-respiratory disorder. When a respiratory disorder such as apnea is detected, the neural stimulation therapy is suspended or adjusted for a lower intensity, or a separate neural stimulation therapy is delivered to treat the detected respiratory disorder. In another embodiment, system 1240 provides the neural stimulation therapy treating the non-respiratory disorder and another therapy treating the detected respiratory disorder. When the respiratory disorder is detected, system 1240 starts the other therapy treating the detected respiratory disorder and/or adjusts the neural stimulation therapy treating the non-respiratory disorder.

Figure 13:
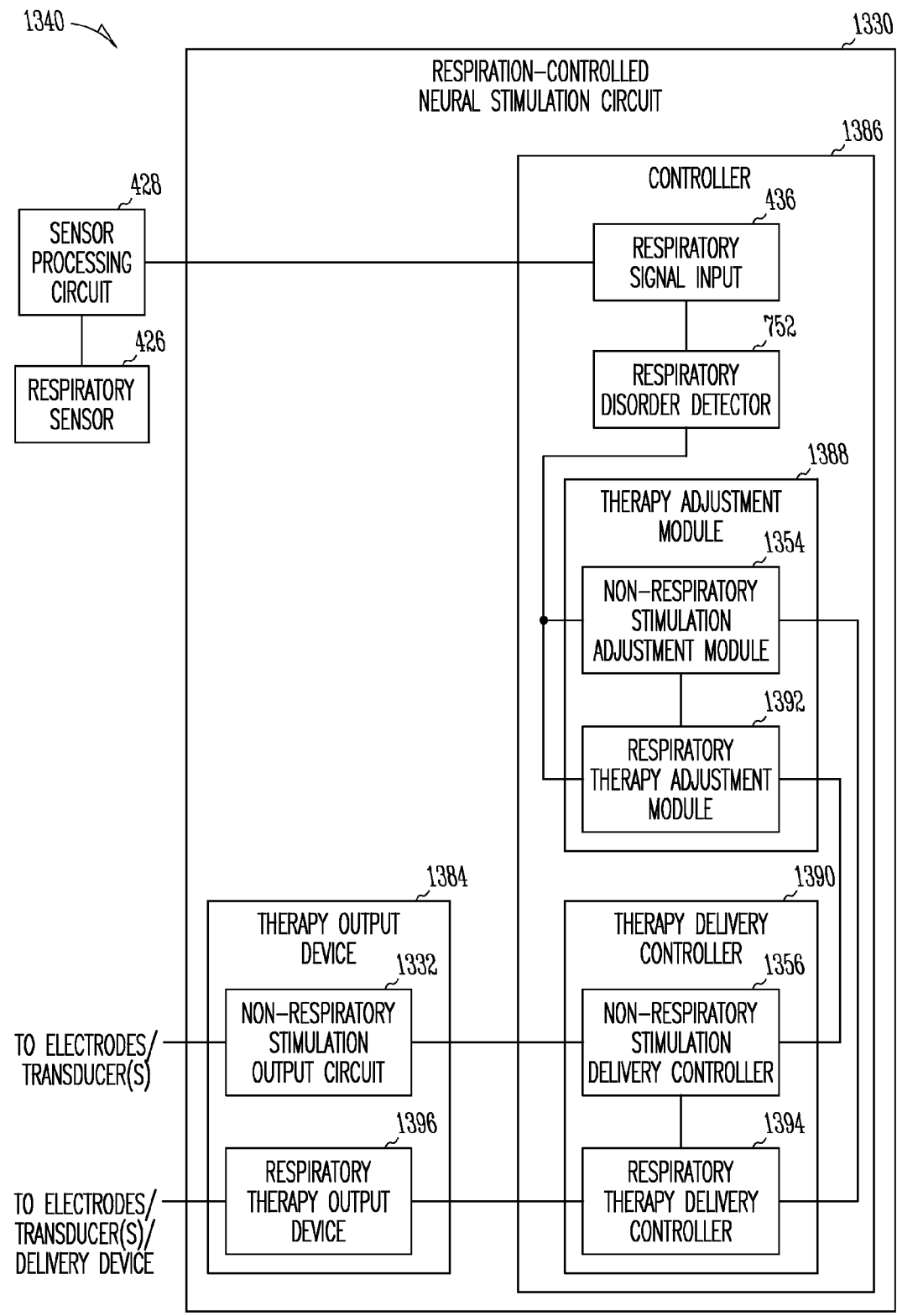
FIG. 13 is a block diagram illustrating a specific embodiment of the respiratory disorder-responsive neural stimulation system of FIG. 12.

FIG. 13 is a block diagram illustrating an embodiment of a respiratory disorder-responsive neural stimulation system 1340, which is a specific embodiment of respiratory disorder-responsive neural stimulation system 1240. System 1340 includes respiratory sensor 426, sensor processing circuit 428, and a respiration-controlled neural stimulation circuit 1330.

Respiration-controlled neural stimulation circuit 1330 is a specific embodiment of respiration-controlled neural stimulation circuit 1230 and includes a therapy output device 1384 and a controller 1386. Therapy output device 1384 includes a non-respiratory stimulation output circuit 1332 and a respiratory therapy output device 1396. Non-respiratory stimulation output circuit 1332 delivers the neural stimulation therapy through electrodes or transducer(s) to treat a non-respiratory disorder, such as a cardiac disorder. Respiratory therapy output device 1396 delivers a respiratory therapy that treats the detected respiratory disorder. In one embodiment, respiratory therapy output device 1396 delivers another neural stimulation therapy through electrodes or transducer(s) to treat the respiratory disorder, such as by stimulating different nerves or nerve branches. Examples of treating respiratory disorders using neural stimulation are discussed in U.S. patent application Ser. No. 11/151,122, entitled "SYSTEM FOR NEURAL CONTROL OF RESPIRATION," filed on Jun. 13, 2005, now issued as U.S. Pat. No. 8,036,750 and U.S. patent application Ser. No. 11/320,500, entitled "NEURAL STIMULATOR TO TREAT SLEEP DISORDERED BREATHING," filed on Dec. 28, 2005, now issued as U.S. Pat. No. 7,672,728, both assigned to Cardiac Pacemakers, Inc., which are incorporated by reference herein in their entirety. In another embodiment, respiratory therapy output device 1396 delivers a therapy treating the respiratory disorder that is other than a neural stimulation therapy. Examples of such therapies treating the respiratory disorder include cardiac pacing therapies and an external pressure therapy. An example of treating respiratory disorders using cardiac pacing is discussed in U.S. patent application Ser. No. 10/798,794, entitled "RATE REGULARIZATION OF CARDIAC PACING FOR DISORDERED BREATHING THERAPY," filed on Mar. 11, 2004, now issued as U.S. Pat. No. 7,336,996, assigned to Cardiac Pacemakers, Inc., which is incorporated by reference herein in its entirety. An example of treating respiratory disorders using an external pressure therapy, delivered by a continuous positive airway pressure (CPAP)

device controlled by an implantable medical device, is discussed in U.S. patent application Ser. No. 10/930,979, entitled "coordinated use of respiratory and cardiac therapies for sleep disordered breathing," filed on Aug. 31, 2004, now issued as U.S. Pat. No. 7,591,265, assigned to Cardiac Pacemakers, Inc., which is incorporated by reference herein in its entirety.

Controller 1386 includes respiratory signal input 436, respiratory disorder detector 752, a therapy adjustment module 1388, and a therapy delivery controller 1390. Therapy adjustment module 1388 includes a non-respiratory stimulation adjustment module 1354 and a respiratory therapy adjustment module 1392 to provide for a coordinated response to each detection of the respiratory disorder by respiratory disorder detector 752. In one embodiment, in response to the detection of the respiratory disorder, respiratory therapy adjustment module 1392 starts the delivery of the respiratory therapy that treats the detected respiratory disorder. If the respiratory disorder is terminated or mitigated to a tolerable degree in response to the delivery of the respiratory therapy, non-respiratory stimulation adjustment module 1354 does not adjust the neural stimulation therapy treating the non-respiratory disorder. If the respiratory disorder is not terminated or mitigated to the tolerable degree in response to the delivery of the respiratory therapy, non-respiratory stimulation adjustment module 1354 stops the delivery, or reduces the intensity, of the stimulation therapy treating the non-respiratory disorder. In another embodiment, in response to the detection of the respiratory disorder, respiratory therapy adjustment module 1392 starts the delivery of the respiratory therapy that treats the detected respiratory disorder, and non-respiratory stimulation adjustment module 1354 stops the delivery, or reduces the intensity, of the stimulation therapy treating the non-respiratory disorder. Non-respiratory stimulation adjustment module 1354 resumes the normal delivery of the stimulation therapy treating the non-respiratory disorder after a predetermined time interval or when the respiratory disorder is no longer detected by respiratory disorder detector 752, such as by restoring stimulation parameters to those used prior to the detection of the respiratory disorder. Therapy delivery controller 1390 includes a non-respiratory stimulation delivery controller 1356 and a respiratory therapy delivery controller 1394. Non-respiratory stimulation delivery controller 1356 controls the delivery of the stimulation therapy treating the non-respiratory disorder using stimulation parameters set and adjusted by non-respiratory stimulation adjustment module 1354. Respiratory therapy delivery controller 1394 controls the delivery of the respiratory therapy treating the detected respiratory disorder using therapy (neural or cardiac stimulation, or other types of therapy) parameters set and adjusted by respiratory therapy adjustment module 1392.

In one embodiment, system 1340 allows for a neural stimulation therapy to be applied to a patient who is otherwise contraindicated for that neural stimulation therapy. For example, vagal nerve stimulation is known to improve hemodynamic performance and/or controlling ventricular remodeling in heart failure patients. However, a substantial percentage of heart failure patients also suffer apnea, and the vagal nerve stimulation may worsen that abnormal respiratory condition. System 1340 potentially allows application of vagal nerve stimulation to these heart failure patients while monitoring or treating the apnea, thereby removing apnea as a contraindication for vagal nerve stimulation. In this embodiment, respiratory disorder detector 752 includes at least apnea detector 862. In a specific embodiment, in addition to responding to the detection of apnea, non-respiratory stimulation adjustment module 1354 provides feedback control of the vagal nerve stimulation improving hemodynamics and/or controlling ventricular remodeling using a non-respiratory physiological parameter as an input. The feedback control functions to maintain the non-respiratory physiological parameter within a target range. For example, non-respiratory stimulation adjustment module 1354 receives cardiac parameters such as the patient's heart rate or heart rate variability and adjusts the intensity of the vagal nerve stimulation to maintain the heart rate or heart rate variability within a target range.

Figure 14:
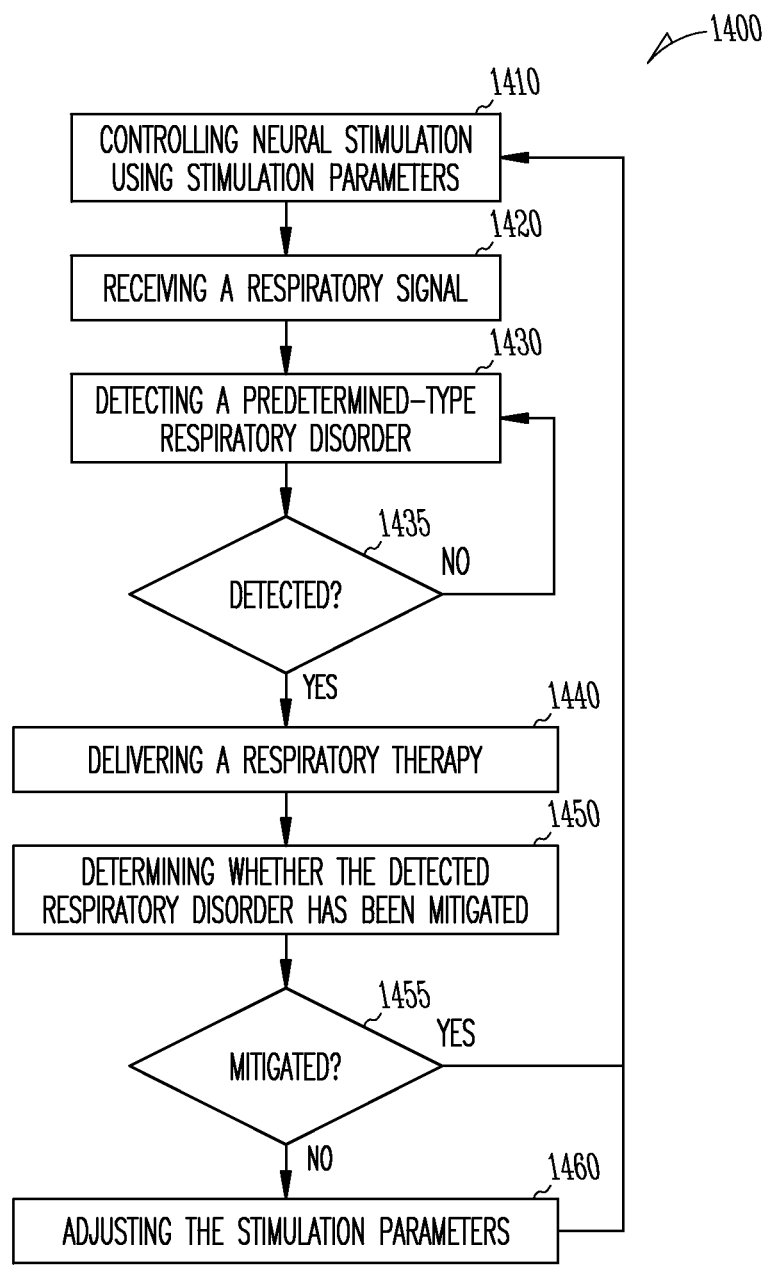
FIG. 14 is a flow chart illustrating an embodiment of a method for responding to a respiratory disorder during neural stimulation.

FIG. 14 is a flow chart illustrating an embodiment of a method 1400 for adjusting neural stimulation in response to the detection of a respiratory disorder. The neural stimulation is a therapy for treating a non-respiratory disorder, such as heart failure. In one embodiment, method 1400 is performed by respiration-controlled neural stimulation circuit 1230 or 1330.

The neural stimulation is controlled by using stimulation parameters at 1410. In one embodiment, the stimulation parameters are selected for treating a cardiac condition, such as to improve hemodynamic performance or control ventricular remodeling in a heart failure patient. A specific embodiment of step 1410 is discussed below, with reference to FIG. 15.

A respiratory signal is received at 1420. The respiratory signal is indicative of respiratory cycles and respiratory parameters. Examples of the respiratory parameters include the respiratory cycle length, the inspiration period, the expiration period, the non-breathing period, the tidal volume, and the minute ventilation. In various embodiments, the respiratory signal is, or is derived from, a physiologic signal indicative of the respiratory cycles and the respiratory parameters. Examples of the physiologic signal include a transthoracic impedance signal and blood pressure signals such as a PAP signal.

A respiratory disorder is being detected at 1430. Examples of the respiratory disorder include abnormal respiratory parameter values such as low respiratory rate, low tidal volume, and low minute ventilation, apnea, hypopnea, and dyspnea. In one embodiment, apnea is detected while the neural stimulation is applied to the heart failure patient.

If the respiratory disorder is detected at 1435, a respiratory therapy is delivered at 1440, to treat the detected respiratory disorder. In one embodiment, the respiratory therapy includes another neural stimulation therapy which uses stimulation parameters selected to treat the detected respiratory disorder. In another embodiment, the respiratory therapy includes one or more therapies other than neural stimulation.

Whether the detected respiratory disorder is mitigated is determined at 1450 by comparing a respiratory parameter to a mitigation threshold. The detected respiratory disorder is considered "mitigated" when its degree is reduced to a tolerable degree at which the detected respiratory disorder is considered not to be harmful to the patient. In various embodiments, the respiratory disorder is detected by comparing the respiratory parameter to a detection threshold, and whether the detected respiratory disorder is mitigated is determined by comparing the respiratory parameter to the mitigation threshold. In one embodiment, the detection threshold and the mitigation threshold are equal. In another embodiment, the detection threshold and the mitigation threshold are substantially different. For example, apnea is detected when the non-breathing period exceeds a detection threshold period, and is determined to be mitigated when the non-breathing period falls below a mitigation threshold period. Hypopnea is detected when the tidal volume is below a detection threshold volume, and is determined to be mitigated when the tidal volume rises above a mitigation threshold volume. Dyspnea is detected when the ratio of the respiratory rate to the tidal volume exceeds a detection threshold ratio, and is determined to be mitigated when that ratio falls below a mitigation threshold ratio.

If it is determined that the detected respiratory disorder has been mitigated at 1455, the neural stimulation is continued to be controlled at 1410 without adjusting the stimulation parameters selected to treat the non-respiratory disorder. If it is determined that the detected respiratory disorder has not been mitigated at 1455, the stimulation parameters are adjusted at 1460 for lowering the intensity, or stopping the delivery, of the neural stimulation for treating the non-respiratory disorder.

Figure 15:
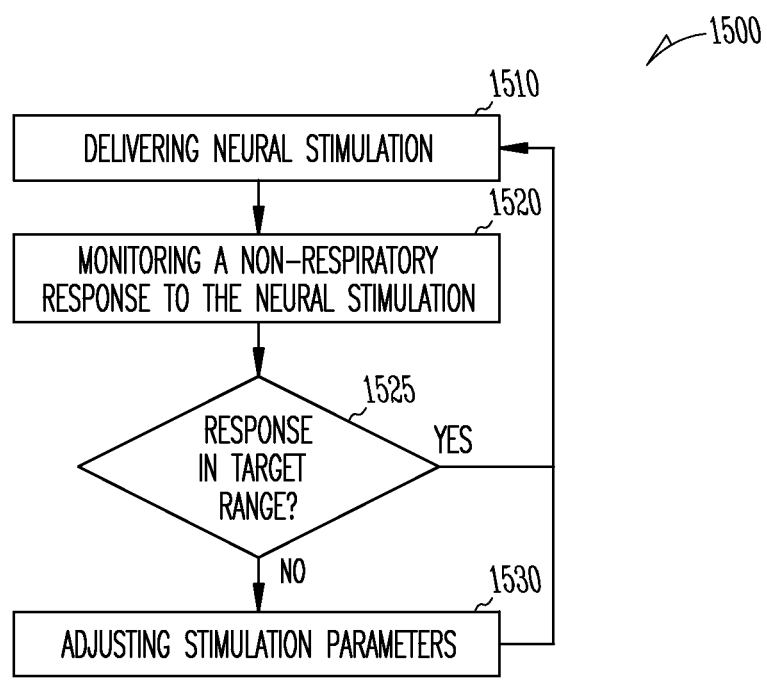
FIG. 15 is a flow chart illustrating an embodiment of a method for controlling a neural stimulation treating a non-respiratory disorder.

FIG. 15 is a flow chart illustrating an embodiment of a method 1500 for controlling the neural stimulation treating the non-respiratory disorder. Method 1500 represents a specific embodiment of step 1410 of method 1400. In one embodiment, method 1500 is performed by non-respiratory stimulation adjustment module 1354.

Method 1500 provides for feedback control of the neural stimulation treating the non-respiratory disorder. The neural stimulation is delivered at 1510, using the stimulation parameters selected to treat the non-respiratory disorder. A non-respiratory response to the neural stimulation is monitored at 1520. If the non-respiratory response is within a target range at 1525, the neural stimulation is continued to be delivered at 1510, without adjusting the stimulation parameters. If the non-respiratory response is not within a target range at 1525, the stimulation parameters are adjusted at 1530, and the neural stimulation is continued to be delivered at 1510 using the adjusted stimulation parameters. In one embodiment, the non-respiratory response is measured by a non-respiratory physiological parameter. For example, for a neural stimulation therapy treating a cardiac disorder, method 1500 is applied to maintain one or more of cardiac parameters such as heart rate, heart rate variability, and blood pressure each within its target range.

With step 1410 performed using method 1500, method 1400 allows the neural stimulation to be adjusted for both treatment of the non-respiratory disorder while limiting potential harm associated with an adverse side effect of the neural stimulation. For example, for a heart failure patient, method 1400 allows the neural stimulation to be adjusted for maintaining a parameter such as heart rate, heart rate variability, or blood pressure within its predetermined target range without causing or worsening a sustained apnea.

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A neural stimulation system, comprising:
an implantable medical device including:
a therapy output device configured to deliver a neural stimulation therapy treating a non-respiratory disorder;
a therapy delivery controller coupled to the therapy output device, the therapy delivery controller configured to control the delivery of the neural stimulation therapy treating the non-respiratory disorder;
a respiratory signal input configured to receive a respiratory signal;
a respiratory disorder detector coupled to the respiratory signal input, the respiratory disorder detector configured to detect a respiratory disorder using the respiratory signal; and
a therapy adjustment module coupled to the therapy delivery controller and the respiratory disorder detector, the therapy adjustment module configured to stop the delivery of the neural stimulation therapy treating the non-respiratory disorder in response to the respiratory disorder being detected and resume the delivery of the neural stimulation therapy treating the non-respiratory disorder in response to the respiratory disorder no longer being detected.

2. The system of claim 1, wherein the respiratory disorder detector is configured to detect the respiratory disorder using the respiratory signal and one or more physiologic signals allowing for determination of whether the respiratory disorder is caused or worsened by vagal nerve stimulation.

3. The system of claim 1, wherein the therapy adjustment module is configured to provide feedback control to the delivery of the neural stimulation therapy treating the non-respiratory disorder using a non-respiratory physiological parameter as an input, the feedback control configured to maintain the non-respiratory physiological parameter within a target range.

4. The system of claim 1, wherein the therapy output device is further configured to deliver a respiratory therapy treating the respiratory disorder, the therapy delivery controller is further configured to control the delivery of the respiratory therapy, and the therapy adjustment module is further configured to start delivery of the respiratory therapy in response to the detection of the respiratory disorder.

5. The system of claim 4, wherein the therapy output circuit is configured to deliver a further neural stimulation therapy treating the respiratory disorder, and the therapy adjustment module is configured to start the further neural stimulation therapy in response to the detection of the respiratory disorder.

6. The system of claim 1, wherein the respiratory signal is indicative of respiratory cycles, and the implantable medical device further comprises a synchronization module coupled to the therapy delivery controller and the respiratory signal input, the synchronization module configured to synchronize the delivery of the neural stimulation therapy treating the non-respiratory disorder to the respiratory cycles.

7. The system of claim 6, wherein the synchronization module comprises:
a respiratory fiducial point detector configured to detect respiratory fiducial points from the respiratory signal; and
a delay timer configured to time a delay interval starting with each of the detected respiratory fiducial points,
and wherein the therapy delivery controller is configured to cause the therapy output circuit to deliver a burst of neural stimulation pulses when the delay interval expires.

8. The system of claim 7, wherein the respiratory fiducial point detector comprises a peak detector configured to detect peaks of the respiratory signal, and the delay timer is configured to time a delay interval starting with each of the detected peaks of the respiratory signal.

9. The system of claim 1, wherein the respiratory disorder detector is configured to detect at least one of apnea, hypopnea, or dyspnea.

10. The system of claim 1, wherein the respiratory disorder detector is configured to detect abnormal values of one or more respiratory parameters including at least one of a respiratory rate, tidal volume, or minute ventilation.

11. A method for neural stimulation, the method comprising:
- delivering a neural stimulation therapy treating a non-respiratory disorder from an implantable medical device;
- sensing a respiratory signal using an implantable respiratory sensor;
- detecting a respiratory disorder using the respiratory signal using the implantable medical device;
- stopping the delivery of the neural stimulation therapy treating the non-respiratory disorder in response to the detection of the respiratory disorder; and
- resuming the delivery of the neural stimulation therapy treating the non-respiratory disorder when the respiratory disorder is no longer detected.

12. The method of claim 11, wherein detecting the respiratory disorder comprises detecting a respiratory disorder induced by the delivery of the neural stimulation therapy treating the non-respiratory disorder.

13. The method of claim 11, further comprising:
- monitoring a non-respiratory response to the delivery of the neural stimulation therapy treating the non-respiratory disorder; and
- adjusting the neural stimulation therapy treating the non-respiratory disorder in response to the non-respiratory response falling out of a target range.

14. The method of claim 11, further comprising delivering a respiratory therapy treating the respiratory disorder, and starting the delivery of the respiratory therapy treating the respiratory disorder in response to the detection of the respiratory disorder.

15. The method of claim 14, wherein delivering the respiratory therapy treating the respiratory disorder comprises delivering a further neural stimulation therapy treating the respiratory disorder.

16. The method of claim 14, wherein delivering the respiratory therapy comprises delivering a cardiac pacing therapy.

17. The method of claim 14, wherein the respiratory signal is indicative of respiratory cycles, and further comprising synchronizing the delivery of the neural stimulation therapy treating the non-respiratory disorder to the respiratory cycles.

18. The method of claim 17, wherein synchronizing the delivery of the neural stimulation therapy treating the non-respiratory disorder to the respiratory cycles comprises:
- detecting predetermined-type respiratory fiducial points from the respiratory signal;
- starting a delay interval with each of the detected predetermined-type respiratory fiducial points; and
- delivering a burst of neural stimulation pulses when the delay interval expires.

19. The method of claim 11, wherein detecting the respiratory disorder comprises detecting at least one of apnea, hypopnea, or dyspnea.

20. The method of claim 11, wherein detecting the respiratory disorder comprises detecting abnormal values of one or more respiratory parameters including at least one of a respiratory rate, tidal volume, or minute ventilation.

* * * * *